(12) United States Patent
Gonzalez

(10) Patent No.: US 12,280,348 B2
(45) Date of Patent: Apr. 22, 2025

(54) AEROGEL BASED ON GAS VESICLES AND BACTERIAL CELLULOSE

(71) Applicant: Lina Gonzalez, Worcester, MA (US)

(72) Inventor: Lina Gonzalez, Worcester, MA (US)

( * ) Notice: Subject to any disclaimer, the term of this patent is extended or adjusted under 35 U.S.C. 154(b) by 0 days.

(21) Appl. No.: 17/391,352

(22) Filed: Aug. 2, 2021

(65) Prior Publication Data
US 2022/0401908 A1    Dec. 22, 2022

Related U.S. Application Data

(60) Provisional application No. 63/059,303, filed on Jul. 31, 2020.

(51) Int. Cl.
| | | |
|---|---|---|
| *B01J 13/00* | (2006.01) | |
| *C08L 1/02* | (2006.01) | |
| *C08L 101/12* | (2006.01) | |
| *C09D 101/08* | (2006.01) | |
| *C12P 19/04* | (2006.01) | |
| *C12P 21/00* | (2006.01) | |
| *C12R 1/02* | (2006.01) | |
| *C12R 1/89* | (2006.01) | |

(52) U.S. Cl.
CPC .............. *B01J 13/0091* (2013.01); *C08L 1/02* (2013.01); *C09D 101/08* (2013.01); *C12P 19/04* (2013.01); *C12P 21/00* (2013.01); *C07K 2319/20* (2013.01); *C08L 101/12* (2013.01); *C12N 2501/998* (2013.01); *C12R 2001/02* (2021.05); *C12R 2001/89* (2021.05)

(58) Field of Classification Search
CPC ....................................................... C08L 1/02
See application file for complete search history.

(56) References Cited

U.S. PATENT DOCUMENTS

| | | | | |
|---|---|---|---|---|
| 2014/0288411 | A1* | 9/2014 | Shapiro .............. | A61K 49/1809 |
| | | | | 530/391.1 |
| 2014/0364381 | A1* | 12/2014 | Ju .......................... | A61L 15/48 |
| | | | | 604/304 |
| 2018/0030501 | A1* | 2/2018 | Bourdeau ................ | C12Q 1/10 |

OTHER PUBLICATIONS

Dassarma et al., "Gas Vesicle Nanoparticles for Antigen Display" Vaccines ISSN2076-393X vol. 3 pp. 686-672 doi:10.3390/vaccines3030686 (Year: 2015).*
Walsby et al., "Gas vesicle proteins" Biochem J vol. 264 pp. 313-322 (Year: 1989).*
Portela et al., "Bacterial cellulose: a versatile biopolymer for wound dressing applications" Microbial Biotechnology vol. 12 No. 4 pp. 586-610 doi:10.1111/1751-7915.13392 (Year: 2019).*
Stergar et al., "Review of aerogel-based materials in biomedical applications" J Sol-Gel Sci Technol vol. 77 pp. 738-752 doi: 10.1007/s10971-016-3968-5 (Year: 2016).*
Honda et al., "Stoichiometrically Controlled Immobilization of Multiple Enzymes on Magnetic Nanoparticles by the Magnetosome Display System for Efficient Cellulose Hydrolysis" Biomacromolecules vol. 16 pp. 3863-3868, DOI: 10.1021/acs.biomac.5b01174 (Year: 2015).*

(Continued)

*Primary Examiner* — Eric Olson
(74) *Attorney, Agent, or Firm* — Prince Lobel Tye LLP

(57) ABSTRACT

A material with a scaffold comprising a series of at least partially spaced fibers and gas vesicles locates between fibers. The gas vesicles comprise external anchoring modules that are effective to anchor the gas vesicles to the fibers.

4 Claims, 10 Drawing Sheets
Specification includes a Sequence Listing.

(56) References Cited

OTHER PUBLICATIONS

Valo et al., "Immobilization of protein-coated drug nanoparticles in nanofibrillar cellulose matrices—Enhanced stability and release" Journal of Controlled Release vol. 156 pp. 390-397, doi:10.1016/j.jconrel.2011.07.016 (Year: 2011).*

Janecek et al., "Structural and evolutionary aspects of two families of non-catalytic domains present in starch and glycogen binding proteins from microbes, plants, and animals" Enzyme and Microbial Technology vol. 49 pp. 429-440, DOI: 10.1016/j.enzmictec.2011.07.002 (Year: 2011).*

Volkner et al., "Accessory Gvp Proteins Form a Complex During Gas Vesicle Formation of Haloarchaea" Frontiers in Microbiology vol. 11 article 610179, doi: 10.3389/fmicb.2020.610179 (Year: 2020).*

\* cited by examiner

SEQUENCE LISTING

```
<160> NUMBER OF SEQ ID NOS: 5

<210> SEQ ID NO 1
<211> LENGTH: 6385
<212> TYPE: DNA
<213> ORGANISM: Artificial Sequence
<220> FEATURE:
<223> OTHER INFORMATION: Synthesized in the lab
<220> FEATURE:
<221> NAME/KEY: promoter
<222> LOCATION: (113)...(147)
<223> OTHER INFORMATION: Anderson promoter J23104
<220> FEATURE:
<221> NAME/KEY: RBS
<222> LOCATION: (177)...(182)
<223> OTHER INFORMATION: Consensus RBS
<220> FEATURE:
<221> NAME/KEY: CDS
<222> LOCATION: (199)...(1222)
<223> OTHER INFORMATION: gene slr1143 from Synechocystis sp. ATCC
      27184D-5
<220> FEATURE:
<221> NAME/KEY: terminator
<222> LOCATION: (1265)...(1359)
<223> OTHER INFORMATION: lambda t0
<220> FEATURE:
<221> NAME/KEY: rep_origin
<222> LOCATION: (5861)...(6255)
<223> OTHER INFORMATION: OriV
<220> FEATURE:
<221> NAME/KEY: backbone
<222> LOCATION: (1360)...(6385)
<223> OTHER INFORMATION: Based on broad host vector RSF1010

<400> SEQUENCE: 1
ttaattaaag cggataacaa tttcacacag gaggccgcct aggccgcggc cgcgcgaatt     60
cgagctcggt acccggggat cctctagagt cgacctgcag gcatgcaagc ttttgacagc    120
tagctcagtc ctaggtattg tgctagcact ctagaaataa ttttgtttat ctctcgagga    180
ggtatactag atggaagcta aattaccgca aaatgaggag caacgcctgg cagttttgag    240
```

```
gcaactcaat attttggata ctcccattga agaaagattt gagcgtatta cccgtatggt    300
ctgccggtcc ctcaaagtgc ccattgccgc catatcaata gttgatgaat cacgccagtg    360
gtttaaatct attcaagggt taaatgcttc cgaaaccccc cgtgaaattg ccttttgcgc    420
ccacgccatc ctcagggatg aattactgtt ggtcgaggat gctacccagg atgaacgctt    480
tgctgacaat cccttggtaa ccgacgagcc tttcatccga ttttatgccg gttatcccct    540
taatttgggt caagatatcc atgtgggaac cctctgcgcc attgatcggg tgccccggga    600
attgtcggcg gaagaacagg aaattctcta cgacctctcc aaaatggtgg agtctgaact    660
ggcggcgatc gccctatcgg aggctcaaat acagctaatt caagaactgg atgaacttga    720
aagggtggcc atggtcgata gcttaacaag actctggaac cgtttgggca ttgaaactct    780
tctaaaacgg gaatgggagt acgctacccg caaaaattct cctatttcca ttgtcatgat    840
tgattttgac aactttaaac aaatcaacga tcaacacggt catttagtcg agacgaggt    900 tctgcagggt agtgcccgtt taatcatttc agttcttcgt tcctacgata ttttgggcag    960
atggggagga gatgagttca tgcttattct gcctggttct ggtcgggagc agaccgctgt   1020
gctcctagaa agaattcaag ccaccattgc ccaaaaccca gtacccacat ctgcgggacc   1080
catggcaatc agcttgagta tggggggagt cagtgtattt accaaccagg gtgaagcact   1140
ccagtattgg gtagaacagg cagataatca gttgatgaaa gtcaaacgtc ttggtaaggg   1200
caattttcaa ctggcagaat aagcggccgc gtcgtgactg ggaaaaccct ggcgactagt   1260
cttggactcc tgttgataga tccagtaatg acctcagaac tccatctgga tttgttcaga   1320
acgctcggtt gccgccgggc gttttttatt ggtgagaatc caggggtccc caataattac   1380
gatttaaatt tgtgtctcaa atctctgatg ttacattgc acaagataaa aatatatcat    1440
catgaacaat aaaactgtct gcttacataa acagtaatac aagggtgtt atgagccata    1500 ttcagcgtga acgagctgt agccgtccgc gtctgaacag caacatggat gcggatctgt    1560
atggctataa atgggcgcgt gataacgtgg gtcagagcgg cgcgaccatt tatcgtctgt   1620
atggcaaacc ggatgcgccg gaactgtttc tgaaacatgg caaaggcagc gtggcgaacg   1680
atgtgaccga tgaaatggtg cgtctgaact ggctgaccga atttatgccg ctgccgacca   1740
ttaaacattt tattcgcacc ccggatgatg cgtggctgct gaccaccgcg attccgggca   1800
aaaccgcgtt tcaggtgctg gaagaatatc cggatagcgg cgaaaacatt gtggatgcgc   1860
tggccgtgtt tctgcgtcgt ctgcatagca ttccggtgtg caactgcccg tttaacagcg   1920
atcgtgtgtt tcgtctggcc caggcgcaga gccgtatgaa caacgcctg gtggatgcga   1980 gcgattttga tgatgaacgt aacggctggc cggtggaaca ggtgtggaaa gaaatgcata   2040
aactgctgcc gttagcccg gatagcgtgg tgacccacgg cgattttagc ctggataacc   2100 tgatttttcga tgaaggcaaa ctgattggct gcattgatgt gggccgtgtg ggcattgcgg   2160
atcgttatca ggatctggcc attctgtgga actgcctggg cgaatttagc ccgagcctgc   2220
aaaaacgtct gtttcagaaa tatggcattg ataatccgga tatgaacaaa ctgcaatttc   2280
atctgatgct ggatgaattt ttctaataat taattggacc gcggtccgcg cgttgtcctt   2340
ttccgctgca taaccctgct tcgggtcat tatagcgatt ttttcggtat atccatcctt   2400
tttcgcacga tatacaggat tttgccaaag ggttcgtgta actttccttt ggtgtatcca   2460
acggcgtcag ccgggcagga taggtgaagt aggcccaccc gcgagcgggt gttccttctt   2520
cactgtccct tattcgcacc tggcggtgct caacgggaat cctgctctgc gaggctggcc   2580
gtaggccggc ctcagcctgc cgccttgggc cgggtgatgt cgtacttgcc cgccgcgaac   2640
```

```
tcggttaccg tccagcccag cgcgaccagc tccggcaacg cctcgcgcac ccgctggcgg    2700
cgcttgcgca tggtcgaacc actggcctct gacggccaga catagccgca caaggtatct    2760
atggaagcct tgccggtttt gccggggtcg atccagccac acagccgctg gtgcagcagg    2820
cgggcggttt cgctgtccag cgcccgcacc tcgtccatgc tgatgcgcac atgctggccg    2880
ccacccatga cggcctgcgc gatcaagggg ttcagggcca cgtacaggcg cccgtccgcc    2940
tcgtcgctgg cgtactccga cagcagccga aaccctgcc gcttgcggcc attctgggcg    3000
atgatggata ccttccaaag gcgctcgatg cagtcctgta tgtgcttgag cgccccacca    3060
ctatcgacct ctgccccgat ttcctttgcc agcgcccgat agctaccttt gaccacatgg    3120
cattcagcgg tgacggcctc ccacttgggt tccaggaaca gccggagctg ccgtccgcct    3180
tcggtcttgg gttccgggcc aagcactagg ccattaggcc cagccatggc caccagccct    3240
tgcaggatgc gcagatcatc agcgcccagc ggctccgggc cgctgaactc gatccgcttg    3300
ccgtcgccgt agtcatacgt cacgtccagc ttgctgcgct tgcgctcgcc ccgcttgagg    3360
gcacggaaca ggccggggc cagacagtgc gccgggtcgt gccggacgtg gctgaggctg    3420
tgcttgttct taggcttcac cacggggcac ccccttgctc ttgcgctgcc tctccagcac    3480
ggcgggcttg agcaccccgc cgtcatgccg cctgaaccac cgatcagcga acggtgcgcc    3540
atagttggcc ttgctcacac cgaagcggac gaagaaccgg cgctggtcgt cgtccacacc    3600
ccattcctcg gcctcggcgc tggtcatgct cgacaggtag gactgccagc ggatgttatc    3660
gaccagtacc gagctgcccc ggctggcctg ctgctggtcg cctgcgccca tcatggccgc    3720
gcccttgctg gcatggtgca ggaacacgat agagcacccg gtatcggcgg cgatggcctc    3780
catgcgaccg atgacctggg ccatggggcc gctggcgttt tcttcctcga tgtggaaccg    3840
gcgcagcgtg tccagcacca tcaggcggcg gccctcgggcg gcgcgcttga ggccgtcgaa    3900
ccactccggg gccatgatgt tgggcaggct gccgatcagc ggctggatca gcaggccgtc    3960
agccacggct tgccgttcct cggcgctgag gtgcgcccca agggcgtgca ggcggtgatg    4020
aatggcggtg ggcgggtctt cggcgggcag gtagatcacc gggccggtgg cagttcgcc    4080 cacctccagc agatccggcc cgcctgcaat ctgtgcggcc agttgcaggg ccagcatgga    4140
tttaccggca ccaccgggcg acaccagcgc cccgaccgta ccggccacca tgttgggcaa    4200
aacgtagtcc agcggtggcg gcgctgctgc gaacgcctcc agaatattga taggcttatg    4260
ggtagccatt gattgcctcc tttgcaggca gttggtggtt aggcgctggc ggggtcacta    4320
cccccgccct gcgccgctct gagttcttcc aggcactcgc gcagcgcctc gtattcgtcg    4380
tcggtcagcc agaacttgcg ctgacgcatc cctttggcct tcatgcgctc ggcatatcgc    4440
gcttggcgta cagcgtcagg gctggccagc aggtcgccgg tctgcttgtc cttttggtct    4500
ttcatatcag tcaccgagaa acttgccggg gccgaaaggc ttgtcttcgc ggaacaagga    4560
caaggtgcag ccgtcaaggt taaggctggc catatcagcg actgaaaagc ggccagcctc    4620
ggccttgttt gacgtataac caaagccacc gggcaaccaa tagcccttgt cacttttgat    4680
caggtagacc gaccctgaag cgcttttttc gtattccata aaaccccctt ctgtgcgtga    4740
gtactcatag tataacaggc gtgagtacca acgcaagcac tacatgctga aatctggccc    4800
gcccctgtcc atgcctcgct ggcggggtgc cggtgcccgt gccagctcgg cccgcgcaag    4860
ctggacgctg gcagaccca tgaccttgct gacggtgcgc tcgatgtaat ccgcttcgtg    4920
gccgggcttg cgctctgcca gcgctgggct ggcctcggcc atggccttgc cgatttcctc    4980
```

| | |
|---|---|
| ggcactgcgg ccccggctgg ccagcttctg cgcggcgata aagtcgcact tgctgaggtc | 5040 |
| atcaccgaag cgcttgacca gcccggccat ctcgctgcgg tactcgtcca gcgccgtgcg | 5100 |
| ccggtggcgg ctaagctgcc gctcgggcag ttcgaggctg ccagcctgc gggccttctc | 5160 |
| ctgctgccgc tgggcctgct cgatctgctg ccagcctgc tgcaccagcg ccgggccagc | 5220 |
| ggtggcggtc ttgcccttgg attcacgcag cagcacccac ggctgataac cggcgcgggt | 5280 |
| ggtgtgcttg tccttgcggt tggtgaagcc cgccaagcgg ccatagtggc ggctgtcggc | 5340 |
| gctggccggg tcggcgtcgt actcgctggc cagcgtccgg gcaatctgcc cccgaagttc | 5400 |
| accgcctgcg gcgtcggcca ccttgaccca tgcctgatag ttcttcgggc tggtttccac | 5460 |
| taccagggca ggctcccggc cctcggcttt catgtcatcc aggtcaaact cgctgaggtc | 5520 |
| gtccaccagc accagaccat gccgctcctg ctcggcgggc ctgatataca cgtcattgcc | 5580 |
| ctgggcattc atccgcttga gccatggcgt gttctggagc acttcggcgg ctgaccattc | 5640 |
| ccggttcatc atctgccgg tggtggcgtc cctgacgccg atatcgaagc gctcacagcc | 5700 |
| catgccttg agctgtcggc ctatggcctg caaagtcctg tcgttcttca tcgggccacc | 5760 |
| aagcgattcc cacacattat acgagccgga agcataaagt gtaaagccta gatccgaagg | 5820 |
| atgagccggg ctgaatgatc gaccgagaca ggccctgcgg ggctgcacac gcgccccac | 5880 |
| ccttcgggta gggggaaagg ccgctaaagc ggctaaaagc gctccagcgt atttctgcgg | 5940 |
| ggtttggtgt ggggtttagc gggctttgcc cgcctttccc cctgccgcgc agcggtgggg | 6000 |
| cggtgtgtag cctagcgcag cgaatagacc agctatccgg cctctggccg ggcatattgg | 6060 |
| gcaagggcag cagcgcccca caagggcgct gataaccgcg cctagtggat tattcttaga | 6120 |
| taatcatgga tggattttc caacaccccg ccagccccg ccctgctgg gtttgcaggt | 6180 |
| ttgggggcgt gacagttatt gcaggggttc gtgacagtta ttgcagggg gcgtgacagt | 6240 |
| tattgcaggg gttcgtgaca gttagggcgc gcccagctgt ctagggcggc ggatttgtcc | 6300 |
| tactcaggag agcgttcacc gacaaacaac agataaaacg aaaggcccag tctttcgact | 6360 |
| gagcctttcg ttttatttga tgcct | 6385 |

```
<210> SEQ ID NO 2
<211> LENGTH: 6365
<212> TYPE: DNA
<213> ORGANISM: Artificial Sequence
<220> FEATURE:
<223> OTHER INFORMATION: Synthesized in the lab
<220> FEATURE:
<221> NAME/KEY: promoter
<222> LOCATION: (93)...(127)
<223> OTHER INFORMATION: Anderson promoter J23108
<220> FEATURE:
<221> NAME/KEY: RBS
<222> LOCATION: (177)...(182)
<223> OTHER INFORMATION: Consensus RBS
<220> FEATURE:
<221> NAME/KEY: CDS
<222> LOCATION: (199)...(1222)
<223> OTHER INFORMATION: gene slr1143 from Synechocystis sp. ATCC
      27184D-5
<220> FEATURE:
<221> NAME/KEY: terminator
<222> LOCATION: (1265)...(1359)
<223> OTHER INFORMATION: lambda t0
<220> FEATURE:
<221> NAME/KEY: rep_origin
<222> LOCATION: (5861)...(6255)
<223> OTHER INFORMATION: OriV
<220> FEATURE:
<221> NAME/KEY: backbone
<222> LOCATION: (1360)...(6385)
```

<223> OTHER INFORMATION: Based on broad host vector RSF1010

<400> SEQUENCE: 2

```
ttaattaaag cggataacaa tttcacacag gaggccgcct aggccgcggc cgcgcgaatt      60
cgagctcggt acccggggat cctctagagt cgctgacagc tagctcagtc ctaggtataa     120
tgctagcact ctagaaataa ttttgtttat ctctcgagga ggtatactag atggaagcta     180
aattaccgca aaatgaggag caacgcctgg cagttttgag caactcaat attttggata      240
ctcccattga agaaagattt gagcgtatta cccgtatggt ctgccggtcc ctcaaagtgc     300
ccattgccgc catatcaata gttgatgaat acgccagtg gtttaaatct attcaagggt      360
taaatgcttc cgaaaccccc cgtgaaattg ccttttgcgc ccacgccatc ctcagggatg     420
aattactgtt ggtcgaggat gctacccagg atgaacgctt tgctgacaat cccttggtaa     480
ccgacgagcc tttcatccga ttttatgccg gttatcccct aatttgggt caagatatcc      540
atgtgggaac cctctgcgcc attgatcggg tgccccggga attgtcggcg aagaacagg      600
aaattctcta cgacctctcc aaaatggtgg agtctgaact ggcggcgatc gccctatcgg     660
aggctcaaat acagctaatt caagaactgg atgaacttga agggtggcc atggtcgata      720
gcttaacaag actctggaac cgtttgggca ttgaaactct tctaaaacgg aatgggagt      780
acgctacccg caaaaattct cctatttcca ttgtcatgat tgattttgac aactttaaac     840
aaatcaacga tcaacacggt catttagtcg agacgaggt tctgcagggt agtgcccgtt      900
taatcatttc agttcttcgt tcctacgata ttttgggcag atggggagga tgagttca      960
tgcttattct gcctggttct ggtcgggagc agaccgctgt gctcctagaa agaattcaag    1020
ccaccattgc ccaaaaccca gtacccacat ctgcgggacc catggcaatc agcttgagta    1080
tggggggagt cagtgtattt accaaccagg gtgaagcact ccagtattgg gtagaacagg    1140
cagataatca gttgatgaaa gtcaaacgtc ttggtaaggg caattttcaa ctggcagaat    1200
aagcggccgc gtcgtgactg gaaaaccct ggcgactagt cttggactcc tgttgataga    1260
tccagtaatg acctcagaac tccatctgga tttgttcaga acgctcggtt gccgccgggc    1320
gttttttatt ggtgagaatc caggggtccc caataattac gatttaaatt tgtgtctcaa    1380
aatctctgat gttacattgc acaagataaa aatatatcat catgaacaat aaaactgtct    1440
gcttacataa acagtaatac aagggtgtt atgagccata ttcagcgtga acgagctgt      1500
agccgtccgc gtctgaacag caacatggat gcggatctgt atggctataa atgggcgcgt    1560
gataacgtgg gtcagagcgg cgcgaccatt tatcgtctgt atggcaaacc ggatgcgccg    1620
gaactgtttc tgaaacatgg caaaggcagc gtggcgaacg atgtgaccga tgaaatggtg    1680
cgtctgaact ggctgaccga atttatgccg ctgccgacca ttaaacattt tattcgcacc    1740
ccggatgatg cgtggctgct gaccaccgcg attccgggca aaaccgcgtt tcaggtgctg    1800
gaagaatatc cggatagcgg cgaaaacatt tggatgcgc tggccgtgtt tctgcgtcgt    1860
ctgcatagca ttccggtgtg caactgcccg tttaacagcg atcgtgtgtt tcgtctggcc    1920
caggcgcaga gccgtatgaa caacggcctg gtggatgcga gcgattttga tgatgaacgt    1980
aacggctggc cggtggaaca ggtgtggaaa gaaatgcata aactgctgcc gtttagcccg    2040
gatagcgtgg tgacccacgg cgattttagc ctggataacc tgattttcga tgaaggcaaa    2100
ctgattggct gcattgatgt gggccgtgtg ggcattgcgg atcgttatca ggatctggcc    2160
attctgtgga actgcctggg cgaatttagc ccgagcctgc aaaaacgtct gtttcagaaa    2220
tatggcattg ataatccgga tatgaacaaa ctgcaatttc atctgatgct ggatgaattt    2280
```

```
ttctaataat taattggacc gcggtccgcg cgttgtcctt ttccgctgca taaccctgct    2340
tcggggtcat tatagcgatt ttttcggtat atccatcctt tttcgcacga tatacaggat    2400
tttgccaaag ggttcgtgta gactttcctt ggtgtatcca acggcgtcag ccgggcagga    2460
taggtgaagt aggcccaccc gcgagcgggt gttccttctt cactgtccct tattcgcacc    2520
tggcggtgct caacgggaat cctgctctgc gaggctggcc gtaggccggc ctcagcctgc    2580
cgccttgggc cgggtgatgt cgtacttgcc cgccgcgaac tcggttaccg tccagcccag    2640
cgcgaccagc tccggcaacg cctcgcgcac ccgctggcgg cgcttgcgca tggtcgaacc    2700
actggcctct gacggccaga catagccgca caaggtatct atggaagcct tgccggtttt    2760
gccggggtcg atccagccac acagccgctg gtgcagcagg cggcggtttt cgctgtccag    2820
cgcccgcacc tcgtccatgc tgatgcgcac atgctggccg ccacccatga cggcctgcgc    2880
gatcaagggg ttcagggcca cgtacaggcg cccgtccgcc tcgtcgctgg cgtactccga    2940
cagcagccga aacccctgcc gcttgcggcc attctgggcg atgatggata ccttccaaag    3000
gcgctcgatg cagtcctgta tgtgcttgag cgccccacca ctatcgacct ctgccccgat    3060
ttcctttgcc agcgcccgat agctacctttt gaccacatgg cattcagcgg tgacggcctc    3120
ccacttgggt tccaggaaca gccggagctg ccgtccgcct tcggtcttgg gttccgggcc    3180
aagcactagg ccattaggcc cagccatggc caccagccct gcaggatgc gcagatcatc    3240 agcgcccagc ggctccgggc cgctgaactc gatccgcttg ccgtcgccgt agtcatacgt    3300
cacgtccagc ttgctgcgct tgcgctcgcc ccgcttgagg gcacggaaca ggccggggc    3360 cagacagtgc gccgggtcgt gccggacgtg gctgaggctg tgcttgttct taggcttcac    3420
cacggggcac cccccttgctc ttgcgctgcc tctccagcac ggcgggcttg agcaccccgc    3480
cgtcatgccg cctgaaccac cgatcagcga acggtgcgcc atagttggcc ttgctcacac    3540
cgaagcggac gaagaaccgg cgctggtcgt cgtccacacc ccattcctcg gcctcggcgc    3600
tggtcatgct cgacaggtag gactgccagc ggatgttatc gaccagtacc gagctgcccc    3660
ggctggcctg ctgctggtcg cctgcgccca tcatggccgc gcccttgctg gcatggtgca    3720
ggaacacgat agagcacccg gtatcggcgg cgatggcctc catgcgaccg atgacctggg    3780
ccatggggcc gctggcgttt tcttcctcga tgtggaaccg gcgcagcgtg tccagcacca    3840
tcaggcggcg gccctcggcg gcgcgcttga ggccgtcgaa ccactccggg gccatgatgt    3900
tgggcaggct gccgatcagc ggctggatca gcaggccgtc agccacggct tgccgttcct    3960
cggcgctgag gtgcgcccca agggcgtgca ggcggtgatg aatggcggtg gcgggtctt    4020 cggcgggcag gtagatcacc gggccggtgg gcagttcgcc cacctccagc agatccggcc    4080
cgcctgcaat ctgtgcggcc agttgcaggg ccagcatgga tttaccggca ccaccgggcg    4140
acaccagcgc cccgaccgta ccggccacca tgttgggcaa aacgtagtcc agcggtggcg    4200
gcgctgctgc gaacgcctcc agaatattga taggcttatg ggtagccatt gattgcctcc    4260
tttgcaggca gttggtggtt aggcgctggc ggggtcacta ccccgccct gcgccgctct    4320 gagttcttcc aggcactcgc gcagcgcctg gtattcgtcg tcggtcagcc agaacttgcg    4380
ctgacgcatc cctttggcct tcatgcgctc ggcatatcgc gcttggcgta cagcgtcagg    4440
gctggccagc aggtcgccgg tctgcttgtc cttttggtct ttcatatcag tcaccgagaa    4500
acttgccggg gccgaaaggc ttgtcttcgc ggaacaagga caaggtgcag ccgtcaaggt    4560
taaggctggc catatcagcg actgaaaagc ggccagcctc ggccttgttt gacgtataac    4620
```

```
caaagccacc gggcaaccaa tagcccttgt cacttttgat caggtagacc gaccctgaag    4680
cgcttttttc gtattccata aaaccccctt ctgtgcgtga gtactcatag tataacaggc    4740
gtgagtacca acgcaagcac tacatgctga atctggccc gccctgtcc atgcctcgct     4800
ggcggggtgc cggtgcccgt gccagctcgg cccgcgcaag ctggacgctg gcagaccca    4860
tgaccttgct gacggtgcgc tcgatgtaat ccgcttcgtg gccgggcttg cgctctgcca   4920
gcgctgggct ggcctcggcc atggccttgc cgatttcctc ggcactgcgg ccccggctgg   4980
ccagcttctg cgcggcgata agtcgcact tgctgaggtc atcaccgaag cgcttgacca    5040
gcccggccat ctcgctgcgg tactcgtcca gcgccgtgcg ccggtggcgg ctaagctgcc   5100
gctcgggcag ttcgaggctg ccagcctgc gggccttctc ctgctgccgc tgggcctgct    5160
cgatctgctg gccagcctgc tgcaccagcg ccgggccagc ggtggcggtc ttgcccttgg   5220
attcacgcag cagcacccac ggctgataac cggcgcgggt ggtgtgcttg tccttgcggt   5280
tggtgaagcc cgccaagcgg ccatagtggc ggctgtcggc gctggccggg tcggcgtcgt   5340
actcgctggc cagcgtccgg gcaatctgcc cccgaagttc accgcctgcg cgtcggcca    5400
ccttgaccca tgcctgatag ttcttcgggc tggtttccac taccagggca ggctcccggc   5460
cctcggcttt catgtcatcc aggtcaaact cgctgaggtc gtccaccagc accagaccat   5520
gccgctcctg ctcggcgggc ctgatataca cgtcattgcc ctgggcattc atccgcttga   5580
gccatggcgt gttctggagc acttcggcgg ctgaccattc ccggttcatc atctggccgg   5640
tggtggcgtc cctgacgccg atatcgaagc gctcacagcc atggccttg agctgtcggc    5700
ctatggcctg caaagtcctg tcgttcttca tcgggccacc aagcgattcc cacacattat   5760
acgagccgga agcataaagt gtaaagccta gatccgaagg atgagccggg ctgaatgatc   5820
gaccgagaca ggccctgcgg ggctgcacac gcgccccac ccttcgggta gggggaaagg    5880
ccgctaaagc ggctaaaagc gctccagcgt atttctgcgg ggtttggtgt ggggtttagc   5940
gggctttgcc cgcctttccc cctgccgcgc agcggtgggg cggtgtgtag cctagcgcag   6000
cgaatagacc agctatccgg cctctggccg ggcatattgg gcaagggcag cagcgcccca   6060
caagggcgct gataaccgcg cctagtggat tattcttaga taatcatgga tggatttttc   6120
caacaccccg ccagcccccg cccctgctgg gtttgcaggt ttggggggcgt gacagttatt   6180
gcaggggttc gtgacagtta ttgcaggggg gcgtgacagt tattgcaggg gttcgtgaca   6240
gttagggcgc gcccagctgt ctagggcggc ggatttgtcc tactcaggag agcgttcacc   6300
gacaaacaac agataaaacg aaaggcccag tctttcgact gagcctttcg ttttatttga   6360
tgcct                                                                6365
```

```
<210> SEQ ID NO 3
<211> LENGTH: 11669
<212> TYPE: DNA
<213> ORGANISM: Artificial Sequence
<220> FEATURE:
<223> OTHER INFORMATION: Synthesized in the lab
<220> FEATURE:
<221> NAME/KEY: rep_origin
<222> LOCATION: (924)...(1469)
<223> OTHER INFORMATION: p15A
<220> FEATURE:
<221> NAME/KEY: misc_recomb
<222> LOCATION: (1513)...(2833)
<223> OTHER INFORMATION: amyE homology back
<220> FEATURE:
<221> NAME/KEY: promoter
<222> LOCATION: (4032)...(4060)
<223> OTHER INFORMATION: Pspank
```

```
<220> FEATURE:
<221> NAME/KEY: RBS
<222> LOCATION: (4074)...(4090)
<223> OTHER INFORMATION: spoVG
<220> FEATURE:
<221> NAME/KEY: CDS
<222> LOCATION: (4091)...(4351)
<223> OTHER INFORMATION: gene gvpA from Bacillus megaterium
<220> FEATURE:
<221> NAME/KEY: CDS
<222> LOCATION: (4369)...(4854)
<223> OTHER INFORMATION: gene gvpP from Bacillus megaterium
<220> FEATURE:
<221> NAME/KEY: CDS
<222> LOCATION: (4872)...(5345)
<223> OTHER INFORMATION: gene gvpQ from Bacillus megaterium
<220> FEATURE:
<221> NAME/KEY: CDS
<222> LOCATION: (5363)...(5629)
<223> OTHER INFORMATION: gene gvpB from Bacillus megaterium
<220> FEATURE:
<221> NAME/KEY: CDS
<222> LOCATION: (5647)...(5913)
<223> OTHER INFORMATION: gene gvpR from Bacillus megaterium
<220> FEATURE:
<221> NAME/KEY: CDS
<222> LOCATION: (5931)...(6857)
<223> OTHER INFORMATION: gene gvpN from Bacillus megaterium
<220> FEATURE:
<221> NAME/KEY: CDS
<222> LOCATION: (6875)...(7642)
<223> OTHER INFORMATION: gene gvpF from Bacillus megaterium
<220> FEATURE:
<221> NAME/KEY: CDS
<222> LOCATION: (7644)...(7910)
<223> OTHER INFORMATION: gene gvpG from Bacillus megaterium
<220> FEATURE:
<221> NAME/KEY: CDS
<222> LOCATION: (7911)...(8720)
<223> OTHER INFORMATION: gene gvpL from Bacillus megaterium
<220> FEATURE:
<221> NAME/KEY: CDS
<222> LOCATION: (8738)...(9025)
<223> OTHER INFORMATION: gene gvpS from Bacillus megaterium
<220> FEATURE:
<221> NAME/KEY: CDS
<222> LOCATION: (8979)...(9263)
<223> OTHER INFORMATION: gene gvpK from Bacillus megaterium
<220> FEATURE:
<221> NAME/KEY: CDS
<222> LOCATION: (9281)...(9583)
<223> OTHER INFORMATION: gene gvpJ from Bacillus megaterium
<220> FEATURE:
<221> NAME/KEY: CDS
<222> LOCATION: (9601)...(10488)
<223> OTHER INFORMATION: gene gvpT from Bacillus megaterium
<220> FEATURE:
<221> NAME/KEY: CDS
<222> LOCATION: (10506)...(10922)
<223> OTHER INFORMATION: gene gvpU from Bacillus megaterium
<220> FEATURE:
<221> NAME/KEY: misc_recomb
<222> LOCATION: (10934)...(11581)
<223> OTHER INFORMATION: amyE homology front

<400> SEQUENCE: 3 tcccttttt    gcggcatttt   gccttcctgt   ttttgctcac   ccagaaacgc   tggtgaaagt      60
aaaagatgct   gaagatcagt   tgggtgcacg   agtgggttac   atcgaactgg   atctcaacag     120
cggtaagatc   cttgagagtt   ttcgccccga   agaacgtttt   ccaatgatga   gcactttaa      180 agttctgcta   tgtggcgcgg   tattatcccg   tgttgacgcc   gggcaagagc   aactcggtcg     240
ccgcatacac   tattctcaga   atgacttggt   tgagtactca   ccagtcacag   aaaagcatct     300
tacggatggc   atgacagtaa   gagaattatg   cagtgctgcc   ataaccatga   gtgataacac     360
```

```
tgcggccaac ttacttctga caacgatcgg aggaccgaag gagctaaccg cttttttgca    420
caacatgggg gatcatgtaa ctcgccttga tcgttgggaa ccggagctga atgaagccat    480
accaaacgac gagcgtgaca ccacgatgcc tgcagcaatg gcaacaacgt tgcgcaaact    540
attaactggc gaactactta ctctagcttc ccggcaacaa ttaatagact ggatggaggc    600
ggataaagtt gcaggaccac ttctgcgctc ggcccttccg gctggctggt ttattgctga    660
taaatctgga gccggtgagc gtgggtcgcg cggtatcatt gcagcactgg ggccagatgg    720
taagccctcc cgtatcgtag ttatctacac gacggggagt caggcaacta tggatgaacg    780
aaatagacag atcgctgaga taggtgcctc actgattaag cattggtaac tgtcagacca    840
agtttactca tatatacttt agattgattt aaaacttcat ttttaattta aaaggatcta    900
ggtgaagatc cttttgata atctttccat aggctccgcc cccctgacaa gcatcacgaa    960
atctgacgct caaatcagtg gtggcgaaac ccgacaggac tataaagata ccaggcgttt   1020 cccctggcg ctccctcgt gcgctctcct gttcctgcct ttcggtttac cggtgtcatt   1080
ccgctgttat ggccgcgttt gtctcattcc acgcctgaca ctcagttccg ggtaggcagt   1140
tcgctccaag ctggactgta tgcacgaacc ccccgttcag tccgaccgct gcgccttatc   1200
cggtaactat cgtcttgagt ccaacccgga agacatgca aaagcaccac tggcagcagc   1260
cactggtaat tgatttagag gagttagtct tgaagtcatg cgccggttaa ggctaaactg   1320
aaaggacaag ttttggtgac tgcgctcctc caagccagtt acctcggttc aaagagttgg   1380
tagctcagag aaccttcgaa aaaccgccct gcaaggcggt ttttttcgttt tcagagcaag   1440 agattacgcg cagaccaaaa cgatctcaag aagatcatct tattaatcag ataaaatatt   1500
tcaagatttg cgtcgcgact aagaaaatgc cgtcaaatcc gctcgccatg acttcactaa   1560
cgatgccttt gaaaatcttc aagttctttt ctactaattc aaggcgtgtc tcaccaggtt   1620
tttggtttgc tccggcgcaa atgcagacaa tatcagcatc cttgcagggt atgtttctct   1680
ttgatgtctt tttgtttgtg aagtatttca catttatatt gtgcaacact tcacaaactt   1740
ttgcaagaga aagttttgt ctgatttatg aacaaaaaag aaaccatcat tgatggtttc   1800
tttcggtaag tcccgtctag ccttgccctc aatggggaag agaaccgctt aagcccgagt   1860
cattatataa accatttagc acgtaatcaa agccaggctg attctgaccg ggcacttggg   1920
cgctgccatt attaaaaatc acttttgcgt tggttgtatc cgtgtccgca ggcagcgtca   1980
gcgtgtaaat tccgtctgca tttttagtca ttggttttcc aggccaagat ccggtcaatt   2040
caattactcg gctcccatca tgtttataga tataagcatt tacctggctc caatgattcg   2100 gatttgata gccgatggtt ttggccgacg ctggatctct tttaacaaaa ctgtatttct   2160
cggtcctcgt tacaccatca ctgttcgttc cttttaacat gatggtgtat gttttgccaa   2220
attggatctc cttttccgat tgtgaattga tctccatcct taaacgcctg tcgtctggtc   2280
cattattgat ttgataaacg gcttttgttg tattcgcatc tgcacgcaag gtaatcgtca   2340
gttgatcatt gaaagaatgt gttacacctg ttttgtaatt ctcaaggaaa acatgaggcg   2400
cttttgcaat atcatcagga taaagcacag ctacagacct ggcattgatc gtgcctgtca   2460
gtttaccatc gttcacttga aatgaacccg ctccagcttt attgtcatac ctgccatcag   2520
gcaattttgt tgccgtattg atagagacag aggatgaacc tgcatttgcc agcacaacgc   2580
catgtgagcc gcgctgattc ataaatatct ggttgtttcc attcgggttc gagagttcct   2640
caggctgtcc agccatcaca ttgtgaaatc tattgaccgc agtgatagcc tgatcttcaa   2700
ataaagcact cccgcgatcg cctatttggc ttttccccgg gaacctcaca ccatttccgc   2760
```

```
ctccctcagg tctggaaaag aaaagaggcg tactgcctga acgagaagct atcaccgccc   2820
agcctaaacg gatgatcccc ctatgcaagg gtttattgtt ttctaaaatc tgattaccaa   2880
ttagaatgaa tatttcccaa atattaaata ataaaacaaa aaaattgaaa aaagtgtttc   2940
caccattttt tcaattttt tataattttt ttaatctgtt atttaaatag tttatagtta   3000
aatttacatt ttcattagtc cattcaatat tctctccaag ataactacga actgctaaca   3060
aaattctctc cctatgttct aatggagaag attcagccac tgcatttccc gcaatatctt   3120
ttggtatgat tttacccgtg tccatagtta aaatcatacg gcataaagtt aatatagagt   3180
tggtttcatc atcctgataa ttatctatta attcctctga cgaatccata atggctcttc   3240
tcacatcaga aaatggaata tcaggtagta attcctctaa gtcataattt ccgtatattc   3300
ttttattttt tcgttttgct tggtaaagca ttatggttaa atctgaattt aattccttct   3360
gaggaatgta tccttgttca taaagctctt gtaaccattc tccataaata aattcttgtt   3420
tgggaggatg attccacggt accatttctt gctgaataat aattgttaat tcaatatatc   3480
gtaagttgct tttatctcct atttttttg aaataggtct aatttttgt ataagtattt   3540 ctttactttg atctgtcaat ggttcagata cgacgactaa aaagtcaaga tcactatttg   3600
gttttagtcc actctcaact cctgatccaa acatgtaagt accaataagg ttatttttta   3660
aatgtttccg aagtatttt ttcactttat taatttgttc gtatgtattc aaatatatcc   3720
tcctcactat tttgattagt acctatttta tatccatagt tgttaattaa ataaacttaa   3780
tttagtttat ttatagattt cattggcttc taaatttttt atctagataa taattatttt   3840
agttaatttt attctagatt atatatgata tgatctttca tttccataaa actaaagtaa   3900
gtgtaaacct attcattgtt ttaaaaatat ctcttgccag tcacgttacg ttattagtta   3960
tagttattat aacatgtatt cacgaacgaa atcgccatt tttcgcaatg gcaagaacgt   4020
tgctcgaggg tttgactta tctacaaggt gtggcataat aagctttcgg ctgaaaggtg   4080
gtgaactact atgtccatcc aaaaatccac tgatagcagt agcttggcgg aagtaataga   4140
tagaatcttg gacaaaggga ttgtaattga tgcctttgcc agagtgagtc ttgtaggtat   4200
agagatatta actattgaag ctcgcgttgt tatcgcatcc gtagacacgt ggttgcgcta   4260
cgcggaagcc gtcggcttgt taactgacaa ggttgaagaa gaaggacttc cagggcgtac   4320
agaagagcgt ggggccgggt tgtcatttta aaaaggtggt gaactactat gtccaccacg   4380
gataataacg tacagagtga gaagcaagaa atcaacaac aggaggagaa aacgcagaac   4440
agtctcaact tagcgatcct cggcggggtg gtgggagcgg gtatcggctt gctcagctct   4500
ccgcaaacaa gtaagaaggt tctctcacgt ctcggccaga gtgagatcgt gagagcgacc   4560
gggcaggaat tacggcgtaa cgcgcaagac attttgacac aacaggcgat gggggccctc   4620
cgccaaactg cgaccggata tttagaaaaa gacaacctta gtaagttatt agctccgaag   4680
aagaagaagg acgatgcgtc aaacgaacaa ggggactcac aggaagaggt atcccagagc   4740
gcagaaatgg aaacttctca atatgaggaa ctcaaggagg aaaataagaa tatgaacgat   4800
caactccaaa gaattgagga gatgttgaac aagttgatgg acgctaagaa ataaaaaggt   4860
ggtgaactac tatggacaag aaagatgtag agaaagccgc tcttaaggcc gggaaaaaga   4920
ttatagacca cacgccggaa cctgtcaaag aaaagattga ggaaaaggta aagagaagg   4980 caaaagagaa gttcgtcgag aagacggagg ggaagctgca agagaaggct aatgaagcat   5040
ctgaaaagtt gcaggagacg aaagaaaaaa acgcccaaaa agtccacggc aagggcgagg   5100
```

```
atgcgaaaga aaaacttcag gacgttcttc tttccgttaa agataagtta tcagatgtga    5160
aagaggcggg ggaaaatttc caggagaagg tgagttcatc agacgataaa gaaaaaagca    5220
aaaataaaag aaaaattaag ggggttaatc aaattaaaaa agccaccgac attaaatctt    5280
ccacaaaaat taagagctct aatgacatta agtcatccac tgacttgaag acgatgggga    5340
gctaaaaagg tggtgaacta ctatgagtat ccaaaagagt acgaactcat ctagccttgc    5400
agaagtcatt gatcgtatct tggacaaggg gattgtcatt gatgcgttcg cacgggtgtc    5460
tgtggttggc atcgagatcc ttacaatcga agcccgcgta gtaatagcaa gcgtagatac    5520
gtggttacgc tacgcggagg cggtgggggct tctgcgtgac gacgtggaag aaaacggtct    5580
gccggagaga tctaactcct ctgaaggtca accgagattt tcaatctaaa aaggtggtga    5640
actactatgg agatcaaaaa gataatgcag gctgtaaacg atttcttcgg tgagcacgtt    5700
gctcctccac acaaaataac ctctgtcgag gcgactgaag atgaaggatg gcgtgttatc    5760
gtcgaggtga tagaggagcg tgaatatatg aaaaagtacg caaaggatga aatgttagga    5820
acctatgaat gtttcttgaa caaagagaaa gaagttatca gcttcaagcg gctcgacgtt    5880
cgctacagat cagctatcgg cattgaggca taaaaaggtg gtgaactact atgacagttc    5940
ttaccgataa gagaaaaaaa ggtagcgtg cgtttattca agacgacgag acgaaagaag    6000
tgctgagccg cgcgctgagc tacttaaagt ccggctatag catccacttt actggtcctg    6060
cgggtggagg aaaaacatcc ctggctagag cgttagcaaa gaaaagaaaa cgtccggtta    6120
tgcttatgca tgggaatcac gaactcaaca acaaagactt gatagggac ttcactggct    6180 atacatcaaa aaaagttatt gaccagtatg tccgctccgt gtacaaaaaa gatgagcaag    6240
tgtccgaaaa ctggcaagac ggcagattat tagaggccgt taagaacgga tacactttga    6300
tttatgatga gtttacgcgc tcaaaaccag cgaccaataa catcttcttg tcaattctgg    6360
aagagggtgt cctcccatta tacggggtga agatgacaga tccgttcgtc cgggtccatc    6420
cagactttcg cgttatattt acatctaacc cggcagagta cgcgggcgtc tacgacacgc    6480
aggacgcatt actcgaccgc cttatcacta tgttcataga ttataaagac atcgatcggg    6540
agacggcaat tttaactgag aaaaccgatg ttgaagaaga cgaagcacgg accatcgtca    6600
ccctggtagc gaacgttcgc aaccgtagtg gagatgagaa cagtagcggt ctgagtctgc    6660
gggcctctct tatgatagcc accttggcaa cccaacagga cattcctatc gacgaagcg    6720 atgaagactt ccagacattg tgcattgaca ttttgcacca tccttttgacg aaatgtctcg    6780 atgaggagaa tgcaaagtca aaggctgaaa agataatatt ggaggagtgt aagaacatag    6840
ataccgagga gaagtaaaaa ggtggtgaac tactatgtct gaaactaatg aaacggggat    6900
ttatattttc tccgcgattc aaaccgacaa agacgaggag ttcggggcag tagaagtcga    6960
gggaaccaaa gctgaaacat tcttgattag atataaggac gccgctatgg tcgcggcaga    7020
agtgccgatg aaaatttatc atccaaatcg gcagaacctg ttgatgcatc agaacgcagt    7080
cgctgcgatc atggacaaaa atgatacagt gataccatt tcatttggaa acgtctttaa    7140
atctaaggaa gacgtcaaag tcctgctcga aaatttatat ccacagtttg agaaactttt    7200 cccgcgata aagggcaaga tagaagtcgg cctcaaggtg attgggaaga aggagtggtt    7260
agagaaaaaa gtaaatgaaa acccggaact ggagaaagta agcgcctcag tgaagggtaa    7320
gtccgaagct gcgggatact acgagagaat acaattggga gggatggcac aaaagatgtt    7380
cacgagcttg caaaaggagg tgaaaacgga cgttttagc cctctcgaag aagccgctga    7440
agctgccaaa gctaacgaac caacaggcga gactatgttg ttgaatgcgt ccttttaat    7500
```

```
caatagagaa gatgaggcca aattcgatga gaaggtgaat gaggcacacg aaaattggaa   7560
ggacaaggcg gacttccatt actccggtcc ttggccggca tataattttg tcaacatacg   7620
tctcaaagtt gaagagaaat aacgtgctgc acaagctggt tactgcccca ataaatcttg   7680
tggtcaaaat cggggaaaaa gtgcaagaag aggccgacaa gcagttgtac gacctgccaa   7740
ctattcaaca gaagttgatt caactgcaaa tgatgtttga attaggagaa atacctgaag   7800
aagcctttca ggaaaaggag gatgaacttc tcatgcgtta tgaaatagcc aagcgtagag   7860
aaatagagca atgggaggaa ctcacacaaa agcggaatga ggagtcatag atgggtgaat   7920
tgctttacct gtacggcctg ataccgacga aagaagccgc ggctatcgaa cctttcccgt   7980
cctacaaagg atttgatgga gagcattctt tatatcctat tgccttcgat caggtcacgg   8040
cggttgtcag taaactggac gcagacacat attccgagaa agtgattcag gagaaaatgg   8100
agcaagacat gtcctggctc caggagaaag cattccatca tcacgagacg gtggcagcct   8160
tgtatgagga atttactatt ataccattga agttctgtac aatctataag ggtgaagaaa   8220
gcctccaggc cgccatagag atcaacaaag agaaaatcga aaactctctt acgttgctcc   8280
agggcaatga ggaatggaat gtaaagatat attgtgatga cactgagttg aaaaaaggca   8340
tctccgaaac caacgaatca gtgaaagcaa agaaacagga aattagccac ctcagccctg   8400
ggcgtcagtt cttcgaaaag aagaaaatag accaactgat cgaaaagag cttgagctgc   8460 ataagaacaa ggtttgtgag gaaatccacg ataagttgaa ggaattgagt ttgtacgact   8520
ccgtcaaaaa gaattggtca aaagacgtta ccggagcagc ggaacaaatg gcatggaata   8580
gcgtgttttt gttgccaagc ttacaaataa caaaattcat aaatgagatt gaggaacttc   8640
agcaacgctt agaaaacaag ggatggaagt tcgaggttac cggaccgtgg cctccgtatc   8700
acttctcatc attcgcgtaa aaaggtggtg aactactatg tccctcaaac agtctatgga   8760
aaataaagac atagctctca tcgatatact ggacgtgatt ctcgacaagg gcgtagcaat   8820
aaagggtgac ttaatcatta gtatcgccgg agttgactta gtctacctgg acctgcgcgt   8880
tcttattagc tctgtggaga cgttggtaca agccaaggaa gggaatcgca agccgatcac   8940
gagtgaacaa tttgacaaac aaaaggaaga gttgatggat gcaaccggtc agccaagcaa   9000
atggacgaat ccacttggat cctgatcaag ccgaacaagg ccttgcccaa ctggtgatga   9060
cggttataga gttgttacgc cagatagtag aacgtcacgc gatgcggcgc gtggaagggg   9120
gaactttaac cgacgaacag atcgaaaatt tgggcatcgc gcttatgaat cttgaggaga   9180
agatggatga attaaaagag gtattcggat tagacgcaga ggaccttaac attgatcttg   9240
gtccattggg tagccttctg taaaaggtg gtgaactact atggctgttg agcacaacat   9300
gcagagcagc accatagttg acgtattaga aaaaatatta gataagggag tggtgatcgc   9360
aggagacatc acagtgggaa tcgcggatgt cgaactctta accataaaga tacgtctcat   9420
tgtggctagt gtggataagg ccaaggagat tggaatggat tggtgggaga acgatcccata  9480 tttgtcttcc aaaggcgcaa ataacaaagc attagaggag gaaaataaga tgctccacga   9540
gcgtctcaag actctcgaag agaagattga gacaaagcgt taaaaaggtg gtgaactact   9600
atggccacgg agactaaatt agataacacc caggcggaga acaaggaaaa caaaaacgcc   9660
gagaacggtt caaaagagaa gaatgggtcc aaagcctcaa agactacctc ctcaggacct   9720
ataaaacggg cagttgcggg ggggattatt ggtgctacga ttgggtatgt tagcactcca   9780
gaaaatcgca agtcattgct tgatcgtata gatacggacg aactgaaatc caaagcatct   9840
```

```
gatttaggga ctaaagtaaa ggagaagagt aaatctagcg tcgcatctct caagacatct    9900
gcaggtagct tattcaaaaa ggacaaggac aaaagtaaag atgacgagga aaatgtaaat    9960
tcatcttcta gtgaaacaga agatgataac gtgcaggaat acgatgagct taaagaagag   10020
aatcagactc tgcaagacag actgtcccaa ctcgaagaaa agatgaacat gcttgttgag   10080
ctgtcactta ataaaaatca ggacgaggaa gctgaggata ctgacagcga tgaagaagag   10140
aacgacgaga atgacgaaaa cgatgaaaac gaacaggatg acgagaatga agaggaaact   10200
tcaaaaccgc gcaaaaaaga taaaaagaa gcggagcagg aagaggaaga agaatctgag    10260
tctgatgagg atagtgagga ggaggaagaa gactcccgct ctaacaagaa aaataagaag   10320
gtaaagacag aggaagagga tgaggatgag tcagaagaag aaaaaaagga ggccaagcca   10380
aaaaagtcca ctgcaaagaa gtctaagaat acgaaggcaa agaaaaacac agacgaagaa   10440
gacgacgaag ccacgtctct ttcatcagag gacgatacta cagcgtaaaa aggtggtgaa   10500
ctactatgtc taccggcct agcttttcta caaaagataa tacattggaa tactttgtaa    10560
aggcaagtaa taaacacggg ttctcacttg acataagcct caatgtaaat ggcgcggtga   10620
tcagtggtac aatgattagc gccaaagaat atttcgacta tttaagcgag acatttgagg   10680
aaggtagcga ggtagcacaa gcattgtcag aacaattctc cttagcttct gaggcctcag   10740
agagtaacgg ggaggcagaa gcccattta tcatctcaa gaatactaag atatattgcg     10800
gcgatagcaa gagtacacca tcaaaaggga agatttttg gagaggtaag atcgccgagg    10860
tagatgggtt tttcctgggc aaaatctctg atgctaaaag tacaagcaag aagagttcct   10920
aaaaatatgt atcttatgta ctatttcgat cagaccagtt tttaatttgt gtgtttccat   10980
gtgtccagtt tggaatactc ttaacctcat tggaaatcgc ggcataatca ctggtggtat   11040
gattgatgac cgcgtcaaca atgaccttta tgccatattc ttcagcggct gcacacattt   11100
ctttaaattc ttgttcagta cctaagtaac ggttgccaat ttgatacgat gtcggctgat   11160
acagccagta ccagttcgac atgctttat ctccttgatt cccttccttt acttggttaa    11220
tcggagatgt ctgaatggct gtatatcctg catcatgaat atccttcata ttgtgtttta   11280
acgtattgaa cgaccaattc catgcatgaa gaatggttcc gcttttgatc gacggtgctg   11340
taagctcatt cgatttgttc gccgtttcag cactcgcagc cgccggtcct gccagaacca   11400
aatgaaacag caataaaaat ccagcgaata acggcagtaa agaggttttg aatcgttttg   11460
caaacattct tgacactcct tatttgattt tttgaagact tacttcggag tcaaaaatcc   11520
ctcttacttc attcttccgc ttcctccttt caaaccgatg tgaagactgg agaatttgt    11580 tcgctcatga gacaataacc ctgataaatg cttcaataat attgaaaaag gaagagtatg   11640
agtattcaac atttccgtgt cgcccttat                                      11669
```

```
<210> SEQ ID NO 4
<211> LENGTH: 3828
<212> TYPE: DNA
<213> ORGANISM: Artificial Sequence
<220> FEATURE:
<223> OTHER INFORMATION: Synthesized in the lab
<220> FEATURE:
<221> NAME/KEY: promoter
<222> LOCATION: (1)...(29)
<223> OTHER INFORMATION: Pspank
<220> FEATURE:
<221> NAME/KEY: RBS
<222> LOCATION: (43)...(59)
<223> OTHER INFORMATION: spoVG
<220> FEATURE:
<221> NAME/KEY: CDS
```

```
<222> LOCATION: (60)...(530)
<223> OTHER INFORMATION: gene gvpQ from Bacillus megaterium (removing
      stop codon) and codon optimized for Bacillus subtilis (synthesized
      in the lab)
<220> FEATURE:
<221> NAME/KEY: linker
<222> LOCATION: (531)...(548)
<223> OTHER INFORMATION: glycine-rich linker was synthesized in the lab
<220> FEATURE:
<221> NAME/KEY: CDS
<222> LOCATION: (549)...(3828)
<223> OTHER INFORMATION: Cellulose binding module (CBM)- CBM48 from
      Micromonas pusilla CCMP1545 (synthesized in the lab)

<400> SEQUENCE: 4
ttgactttat ctacaaggtg tggcataata agctttcggc tgaaaggtgg tgaactacta      60
tggacaagaa agatgtagag aaagccgctc ttaaggccgg aaaaagatt  atagaccaca     120 cgccggaacc tgtcaaagaa aagattgagg aaaaggtaaa agagaaggca aaagagaagt     180
tcgtcgagaa gacggagggg aagctgcaag agaaggctaa tgaagcatct gaaaagttgc     240
aggagacgaa agaaaaaaac gcccaaaaag tccacggcaa gggcgaggat gcgaaagaaa     300
aacttcagga cgttcttctt tccgttaaag ataagttatc agatgtgaaa gaggcggggg     360
aaaatttcca ggagaaggtg agttcatcag acgataaaga aaaaagcaaa aataaaagaa     420
aaattaaggg ggttaatcaa attaaaaaag ccaccgacat taaatcttcc acaaaaatta     480
agagctctaa tgacattaag tcatccactg acttgaagac gatggggagc ggtggcggcg     540
gtggtggagg ccacgacggc gcggacgcgt ccagctcgc  gagagcgacg ctccacgagc     600
gcgtcgacgc gaagctccgc gaggcgacgg cggcgacggc gacgcgacga cgccgcggcg     660
gcggcgtcga gctcacggac gagatcgtcg agcgcgcgat gcgcgaggcg ataacggaac     720
tcgacgaagc gtttctcgcg acgcgcgccc cggcggaaac gaccgtcgtc gccgcgttga     780
tgcgcggccg cgacgtctgg atcgcgcacg tgggtgactc gcgcgcgttc gcgtgctcgc     840
cccgtcgcga ccgcggcctc acctccgccg ccgccgcgtc gccgccgccg ccctctccct     900
cgcgccgcgc gccgccgttc gcggccgcgc ggctgacgcg cgaccacgcg ccggacgacc     960
cggccgagcg cgccgcggatc gaacgcgcgg cggcggcgt cgtcgtcgcc ggcgggacgc    1020
cgcgcgtcaa cggcgagctc gcggtgaggt gcgttctata cactggcccc catacgaccg    1080
cgttggcgtg gtgaacgccg atccttaagg acttttgccg gcgcatctct ccgctcatcc    1140
ctcgctttca acgcccgccc tcggcgcctt tcaactccac ctgacgcctt tgaactccac    1200
tccgacattc gctcgtatgg aacgaccctg agccgcgcgg tgggcgacgg cgcgctgcgg    1260
cggtacggcg tcgtcgcgaa cgcgaccgtg tcttcgcgcg tgtcgctcgg ggaggacgac    1320
gcgatcgtgc tcgtgtccga cggcgtatcc gacgtgctcg ccggcgacga ggcgtgttcg    1380
ctcgcgctcg gcggcggcga cggggaggcg gaggagaacc acgcgcgtcg atggacgctg    1440
cgcgacctcg aggcgtggcg cggcgcgcgc acggagacgg ccgcgggagg cgatatcatc    1500
gcgctgggcg ggaccgccgc ggggcggctg cccggggagg aacgcgacgg cgacgacgac    1560
gcgtccggcg gcggcggcgg cggcggcggc ggcgacgacg cgtccgcggc gtggcgaacg    1620
cccacggagg tcgcgtcct  cgcgcggctg aggctcggcg ccgcgacggc ggcgcgcgcg    1680
gcgatgctga tgaacagcgg cgataacgtc gcggtgctcg tgatgacggc gaaggagccg    1740
ccgccgcctt tggacgtcgc gccgcccacg ccgccgccgc cgccgccggc ggccgcggcg    1800
gaagttgaaa cgtcgaccgc cgcggcggac gacgagcgcg cgctcgtcgc gctcgacgcc    1860
gcgctccgcg tgcgcgtcgg cacgacgctc gcgccgcgga cgtgcgacgt cgcgacgacc    1920
```

```
ggccaagacg cggaggacgg cggcggcggg acggggacgt gcgtcgcgtt caacctccgc    1980
cgcgtcgtcg cgttgacgtc cgggccgtac ccgtcgtcgt ccgtcgctca cgcggacgac    2040
gtcgacgtcg cgcgggggga ggacgagctc gaactcggag acgggaccga ggagagcggc    2100
ggcggcggcg gcgcggcgg gtgggacgag ctcgacggcc tgaccgcggg ctccgcgctc    2160
aagttcttct cgagggtgcc agcgaacgcg ttgacgcccg gcgacggcgg cggcggcggc    2220
ggggagcgcc gcgcgacgaa gccgacgacg agcgtcccgg ggaaggaagt cgccgtcgtc    2280
gcgcggttct tggagacccct cggcggcgtc ccgctgcgtc gcgcggggga gacgagtcgc    2340
gcgcgcggcg gcgcggcgg cggcggcggc ggcgacgcgc gcgcggggga gacgggaggg    2400
tatcgcggcg ccgggggggcg gccgttctcg cgcgggcact tcggcgaggt gtggcgcgcg    2460
acagcggcgc gcgcggcggc gtccgacgcc gagaccgacg acgcgaccga cgacgcgacc    2520
gcgacgcggt acgtcctgaa gcgcatcctc gtcgagcgcg gggaggacgt ccgcctgagc    2580
ggccgacgcg aggcgcactt tggcgaggcg attcgagcgg cgacgcgctc cgcggagggt    2640
cgagcgcacc ccggcgcggg gcacgtcgcg cggtacgagt ccacgttcga gatcagaggc    2700
ggcgacggcg gcgacgcggc ggaggacgag ctctggctcg tgttccgcga cgagggcgac    2760
gcgctgtcgt cgctgatgta cgcggacggc gacgacgacg acgacgacgg cgacggcgac    2820
gacgacgaaa aagtcttctc cgcgtcttct ctccgcgtcg tgcgcccatc gcggtggtgg    2880
ctcgaccgcc gcgcgtcgcc gcgcgggcgc cggcggctgc gcgagctcat caggcagacg    2940
atcgccgcgt gcgcgctgac gcacgcgctc ggcgtcgggc atcgagacgt gaagccgagc    3000
aacttgctcg tgtcgtcgtc gtccggcggc ggcgacggat cccccgtcga ccgagaggag    3060
acgcttcggc tcgcggactt tggctccgcg gtcgacgcgc ggtcgctccg tgagctgtac    3120
ggcgacgacg gccccaccgc ggcgcagcag acgccggagt acgcgccgcc ggagagtctg    3180
ttcgacggca tcccgctgca tcacgggacg tcgtcgtcgt ccgtgtcgac gacggcgctg    3240
ggggcggcgc gccggggtcg ccgcgccgcc gccgcctccg gcccgggtga cccggacgcc    3300
gcggacgacg tcgcgaacga cgtcgcgaag gtcgccgcgt acgacatgtg gtccgtgggg    3360
gttctgtccc tcgaggttct cgcgttaggg acgccgaagg tgttcgcgtc cgtcggccgt    3420
cgcacgcgct cggaggtgga gcgtcggctc cgcggcgcga gcgcggagac gaaagagatc    3480
gccgtgcgtc tccgcgcgat gctcgaactg tgcgtgttcc cacccgagcg cggcgtcgcg    3540
gtgatgctgt cctgggagtg caccgaggac gcgctgacgc ggacgatcgc ggcgcgcgac    3600
cctctcggct tggggttgcc gagcgcgtgg gcgctgcgtc tgattcggcg gctgctgtcg    3660
tgggatccgg gcgaccgacc gagcgcggag gaggcgctga cgcacgcgtt ctttcgcgac    3720
gacgacagcg gcgacgcgat cgggcggggg tacgcgtgcg cggagacggg cgcggagttt    3780
gagttcaggc gcgagtgcga ggagcactgc ggccgcgcgt gcgattga              3828
```

<210> SEQ ID NO 5
<211> LENGTH: 824
<212> TYPE: DNA
<213> ORGANISM: Artificial Sequence
<220> FEATURE:
<223> OTHER INFORMATION: Synthesized in the lab
<220> FEATURE:
<221> NAME/KEY: promoter
<222> LOCATION: (1)...(29)
<223> OTHER INFORMATION: Pspank
<220> FEATURE:
<221> NAME/KEY: RBS
<222> LOCATION: (43)...(59)

```
<223> OTHER INFORMATION: spoVG
<220> FEATURE:
<221> NAME/KEY: CDS
<222> LOCATION: (60)...(530)
<223> OTHER INFORMATION: gene gvpQ from Bacillus megaterium (removing
      stop codon) and codon optimized for Bacillus subtilis (synthesized
      in the lab)
<220> FEATURE:
<221> NAME/KEY: linker
<222> LOCATION: (531)...(548)
<223> OTHER INFORMATION: glycine-rich linker was synthesized in the lab
<220> FEATURE:
<221> NAME/KEY: CDS
<222> LOCATION: (549)...(3828)
<223> OTHER INFORMATION: gene bslA from Bacillus subtilis 168
      (synthesized in the lab)

<400> SEQUENCE: 5
ttgactttat ctacaaggtg tggcataata agctttcggc tgaaaggtgg tgaactacta        60
tggacaagaa agatgtagag aaagccgctc ttaaggccgg gaaaaagatt atagaccaca       120
cgccggaacc tgtcaaagaa aagattgagg aaaaggtaaa agagaaggca aaagagaagt       180
tcgtcgagaa gacggagggg aagctgcaag agaaggctaa tgaagcatct gaaaagttgc       240
aggagacgaa agaaaaaaac gcccaaaaag tccacggcaa gggcgaggat gcgaaagaaa       300
aacttcagga cgttcttctt tccgttaaag ataagttatc agatgtgaaa gaggcggggg       360
aaaatttcca ggagaaggtg agttcatcag acgataaaga aaaaagcaaa aataaaagaa       420
aaattaaggg ggttaatcaa attaaaaaag ccaccgacat taaatcttcc acaaaaatta       480
agagctctaa tgacattaag tcatccactg acttgaagac gatggggagc ggtggcggcg       540
gtggtggaat ggtgaccaaa tggattcaga acctgagcca gagcgatctg gcgctgctga       600
aaaactttgt ggtgcagagc ggcaacatta aaagcctgag cgcgcagtat agcgtgagct       660
atccgaccat gcgcgcgcgc ctggataccc tgattgaaaa aattaaaatt ggcgatgaag       720
aaccggatac ctttattgcg cagctgcagg cgtatgcgat tgatcgcaaa gtgccgagcc       780
agtttgtgca ggaaattgcg gaatttatt atacccgcaa agaa                        824
```

AEROGEL BASED ON GAS VESICLES AND BACTERIAL CELLULOSE

CROSS-REFERENCE TO RELATED APPLICATION

This application claims priority of Provisional Patent Application Ser. No. 63/059,303 filed on Jul. 31, 2020, the disclosure of which is incorporated herein by reference in its entirety.

GOVERNMENT RIGHTS

This invention was made with government support under Award ID 2050101 awarded by the National Science Foundation (NSF). The government has certain rights in the invention.

BACKGROUND

This disclosure relates to an aerogel.

Bacterial cellulose (BC) has played an important role in the bioeconomy, specifically in the medical and the food industries. Its roles stem from its high-water retention capacity, biocompatibility, resistance to biodegradation and high purity. Specifically, there are a wealth of applications in the medical field such as skin care, skin tissue repair, artificial dura matter, blood vessels and connective tissues. For example, this BC material helps accelerate the rate of healing mimicking the body extracellular matrix (ECM) and the never-dried wound provides cooling and therefore burn pain relief. Other non-biomedical applications include using the cellulose network as a carrier for catalytic reactions for adsorption of oil spills in aquatic environments, and for making moisturizing facial masks (BOWIL Biotech). In food applications, it has been used as a low-calorie and high-fibre food additive to emulsify, stabilize and modify texture. BC has been used to make nata de coco, sweetened jelly-like cubes that originated in the Philippines. Due to its high thermal resistance (up to 300° C.) it can withstand the processing temperatures of electronics devices and, thus it can be used as a dielectric spacer in semiconductors. BC's strength and lightweight allowed Sony to use it as a speaker diaphragm in headphones.

Gluconoacetobacter *xylinus* is known as the most prolific cellulose producer. In a concerted manner and via a sophisticated glycosyltransferase (GT) molecular machinery, this organism spins out single glucan chains while UDP-glucose are fed, assembled and translocated through tiny pores normal to the cell membrane. There is a hierarchical architecture in the formation of cellulose mat with single glucan chains or elementary fibrils (1.5-3.5 nm) forming microfibrils (10-30 nm) which are subsequently organized into stiff bundled fibers in the order of 100 nm as the bacteria concomitantly undergoes cells division. It is speculated that these cells may be polymerizing ~200,000 glucose units per sec, per cell.

Cellulose extracted from trees contains other compounds such as lignin and hemicellulose that act as the glue that holds the cellulose fibers together. Artificial interpenetrating cellulose networks have been made specifically to reinforce the cellulose network with carbon nanotubes. To name a few, calcium deficient hydroxyapatite, acrylic acid (AAc), soy protein isolate and nanosilver have been incorporated into the cellulose network with resultant applications in bone colonization, heavy metal waste purification, and to prevent wound infections, respectively.

SUMMARY

Disclosed herein is the use of bacterial cellulose as the structural support for making an insulation material.

Bacterial cellulose (BC) serves as a scaffold material for an aerogel, and provides the structural integrity needed for the product to prevent slumping or to maintain it in an upright position. At the same time, this material is compliant and moldable so as to fit into a stud cavity. BC has a young's modulus ~138 GPa and tensile strength of 2 GPa (on par with Kevlar fibers). Gas vesicles can be incorporated into the cellulose network, forming a new composite material with a functional architecture.

The cellulose network is already porous (254±76.65 nm), but having the gas vesicles embedded in them further constrict the size of the pores throughout the material, making it an effective insulator. Essentially, this method permits the anchoring of the fibers and help close the larger gaps in the cellulose network with the gas vesicle acting as the molding "receptacles". Using genetic engineering tools will provide a flexible platform for modifying the scaffold and gas vesicles with the necessary chemistries.

Gas vesicles allow positioning of the *Halobacterium salinarum* cells within an optimal water column for nutrients and gasses. Cell exposed to oxygen limiting conditions upregulates the gas vesicle synthesis. In the photosynthetic bacteria, *Anabaena flos-aquae*, carbohydrate synthesis serves as ballast, while gas vesicles act as buoyant devices to rise these organisms to the surface where light is available. Gasses diffuse freely into the gas vesicles, but they are impermeable to water due to the high surface tension of the hydrophobic interior. The gas vesicles are cylindrical with conical caps or ends with an aspect ratio of approximately 2:1 (length to diameter) and lengths ranging from 0.1 to 2 μm. Thus, creating a process to selectively use vesicles on the order of the mean free path of air molecules (about 68 nm) could provide an R-value near that of an aerogel (R-value~10° F. $ft^2$ h/BTU). Gas vesicles have been used in biotechnology as image contrast agents in MRI.

Two of the well-studied genes responsible for the structural compositions of the gas vesicles are gvpA and gvpC. The GvpA protein acts as ribs for the cylindrical cage and the GvpC protein strengthen the gas vesicles by providing an exterior mesh. This mesh increases the pressure needed to collapse the compartment. The GvpA protein of these vesicles acts as the "ribs" with α-helices and/3-turns and the wall thickness of these vesicles is 2 nm. Using synthetic biology tools, the structural genes, gvpC and gvpA, can be modified to display a cellulose binding domain to secure the vesicles to the fibers.

Essentially, what has been fabricated with these biological organisms are porous structures or a special kind of aerogel. Aerogel was invented in the year 1931, but due to the cost of production its wide used and availability has been hampered. Aerogels are composed of mostly air (>90% porosity) and possess a thermal conductivity lower than that of air as the gasses have a tough time diffusing through the nanoporous cavities (<70 nm). Aerogels are extremely light with density between 0.001 and 0.2 $g/cm^3$ and have high specific surface area between 200 and 600 $m^2/g$. Aerogels have been used by NASA during the Mars Exploration to keep the rover vehicle from losing heat and in the Startdust spacecraft as a collector to trap high speed interstellar particles. In the oil industry, aerogel play a crucial role as a lightweight insulator for oil pipes with a pipe-in-pipe configuration for underwater mining. As a result of having excellent thermal insulation properties, a thin piece of aerogel is sufficient to assures the fluidity of the oil in the freezing cold water. At the same time, it reduces the weight of the pipelines, thus prevents a boat from capsizing. Aerogels are specially desire where a thin piece of insulation is needed or where space is limited. Due to the large surface specific area, aerogels are widely used in adsorption applications.

To make an aerogel and prevent collapsing and shrinkage due to capillary forces either supercritical drying or freeze-drying methods are used. In supercritical drying, solvent exchange is implemented. With such, water is replaced by a solvent (e.g. ethanol) and the material is then subjected to purging with $CO_2$. When a critical high pressure is reached, $CO_2$ completely dissolved in the solvent which lower the liquid gas interfacial forces to zero. At this point, the solvent can be removed without dragging the walls and retaining the 3D structural network.

Instead of replacing the liquid with gasses as it is done with $CO_2$ in supercritical drying and with sublimation as in freeze-drying, in our method, the gasses are already present in the material. Integrating gas vesicles in the media is a completely new method to create open porous network. Cellulose has a high-water retention capacity thus in a sense through genetic engineering (through changing the surface chemistry), the capacity of the network to retain water was altered so as to retain air (gas vesicles) instead. The envelop of the gas vesicles serves as an interphase for conducting the necessary chemistries. In essence, the material will not have to dry the material due to its hydrophobic properties and its residence at the boundary due to its acquired buoyancy.

All examples and features mentioned below can be combined in any technically possible way.

In one aspect, a material includes a scaffold comprising a series of at least partially spaced fibers, and gas vesicles locates between fibers. The gas vesicles comprise external anchoring modules that are effective to anchor the gas vesicles to the fibers.

Some examples include one of the above and/or below features, or any combination thereof. In an example the material is an aerogel. In an example the scaffold comprises bacterial cellulose. In an example the bacterial cellulose is produced by a genetically modified bacterium. In an example the external anchoring modules of the gas vesicles comprise cellulose binding modules. In an example the cellulose binding modules comprise CBM48 from *Komagataeibacter sucrofermentans* and *Micromonas pusilla*. In an example the gas vesicles further comprise external hydrophobicity modules. In an example the gas vesicles further comprise external fire resistance modules.

In another aspect a method of creating gas vesicles includes using a genetically-modified bacterium to produce gas vesicles that comprise external anchoring modules that are effective to anchor the gas vesicles to fibers.

Some examples include one of the above and/or below features, or any combination thereof. In an example the gas vesicles further comprise external hydrophobicity modules. In an example the gas vesicles further comprise external fire resistance modules.

In another aspect, a biodegradable plastic material includes at least one layer of cellulose derived from a bacterial strain, wherein at least one layer is treated with a plasticizer and dried.

Some examples include one of the above and/or below features, or any combination thereof. In an example the plasticizer comprises glycerol. In an example the plasticizer has a glycerol content of up to 1%. Further included is a material made from stacked layers of this plastic material.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the inventions. In the figures, identical or nearly identical components illustrated in various figures may be represented by a like reference character or numeral. For purposes of clarity, not every component may be labeled in every figure. In the figures:

FIG. 1a: Assembled fibers and gas vesicles FIG. 1b: genetically engineering a gas vesicle platform to have CBD, hydrophobicity and fire-retardant properties.

FIG. 3a: circuit diagram of RSF1010 origin vector with the sfgfp gene FIG. 3b: Anderson's promoters (J23XXX) tested in this vector and expressed in *G. xylinus * FIG. 3c: Electroporation transformation efficiency in *G. xylinus*.

* FIG. 4a: circuit diagram with the slr1143 gene driven with the Anderson promoters FIG. 4b: Growth curve of engineered *G. xylinus* strains Gx 60, Gx61 and Gx216 and comparison against the wild type strains FIG. 4c: Cellulose production quantification before and after drying the samples.

FIG. 9a: gvp gene cluster FIG. 9b: Cuminic acid circuit to tune expression of chimeric protein. FIG. 9c: Production, lysis and self-assembly of genetically modified gas vesicles within the cellulose fibers.

FIG. 10a: Construct to modify the fibers with BslA FIG. 10b: Construct to modify the vesicles FIG. 10c: Assembly after secretion of protein complex into the media.

DETAILED DESCRIPTION

Figure 1A:
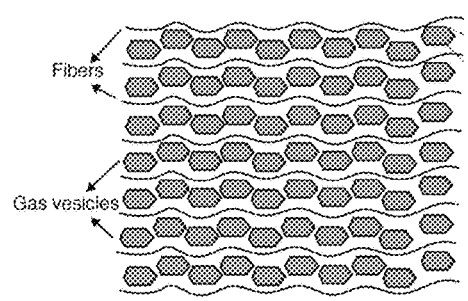
FIGS. 1a-1b. Gas vesicles and cellulose hybrid material.
Figure 1B:
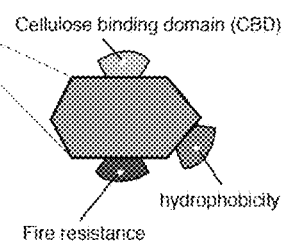

A method includes the development of a green insulation composite material that merges two biologically sourced materials: bacterial cellulose and gas vesicles (FIG. 1a). Fundamentally, the aerogel is made almost entirely out of biological organisms. An incentive to work on these materials is to step away from using non-renewable petroleum-based polymers and toxic products. Both of these biological derived materials have a set of unique properties rendering them suitable for attaining the sought-after properties (insulating, strength to support itself and degree of pliability). Furthermore, both of these materials can be genetically modified to bring desired features to comply with regulations (FIG. 1b). A low thermal conductivity ($\lambda_{eff}$<25 mW/mK) and high R-value are critical parameters to develop a high-performance building insulation material. This will allow to develop an R-value close or higher than R-6. Properties that should be achieved (in addition to thermal performance) are hydrophobicity (to prevent mold growth) and fire resistance. Normally, a separate vapor barrier is applied on the outer layer of an insulation material to keep it dry as insulation properties deteriorate when a material absorbs water.

Part 1: Establish chassis strains and work toward optimizing cellulose production.

Part 2: Add CBD to the gas vesicles to effectively anchor them to the cellulose fibers.

Part 3: Genetically engineering hydrophobicity and fire-retardant properties into the fibers.

Part 1: Establish chassis strains and work toward optimizing cellulose production.

Culture Set-Up for Growing the Hybrid Material and Optimization of SCOBY Culturing Conditions.

There is an immense yield to field advantage in using bacterial cellulose. For example, in a standard soccer field (70 m by 100 m), planted with trees would take 12-18 years before they can be harvested, and it would yield 3.5 tons of cellulose pulp after purification. Considering the same field size, culturing cellulose would take 10-15 days and yield 115 tons of cellulose. Moreover, arable land, fertilizer, pesticide, sunlight and the enormous amount of water used for growing trees are not needed. Moreover, the harsh downstream processing to remove lignin and hemicellulose are not required in the case of bacterial cellulose. Plant crops cannot be vertically stacked for growth whereas cellulose can as they do not require sunlight or direct contact with the soil.

Efforts have been made in replacing the commonly used expensive media, the Hestrin and Schramm (HS) media. At the moment the most economical and practical approach to grow bacterial cellulose is through using a symbiotic culture of bacteria and yeast (SCOBY). SCOBY is used to make a drink called Kombucha which it is popular due to its antioxidant properties, probiotic benefits and propensity to reduce blood sugar level in Type 2 diabetes individuals. Using a SCOBY culture media eliminates the costly ingredient such as the yeast extract (the nitrogen source) used to prepare the HS media. The co-culture can be grown in readily available ingredients such as tea, sugar and apple cider. In the present disclosure the SCOBY recipe is used, adjusting the parameters such as tea type and pH. Only G. xylinus strains are grown, so as to increase the bacterial cellulose yield and avoid the growth of other sugar-consuming organism within the culture.

Figure 2:
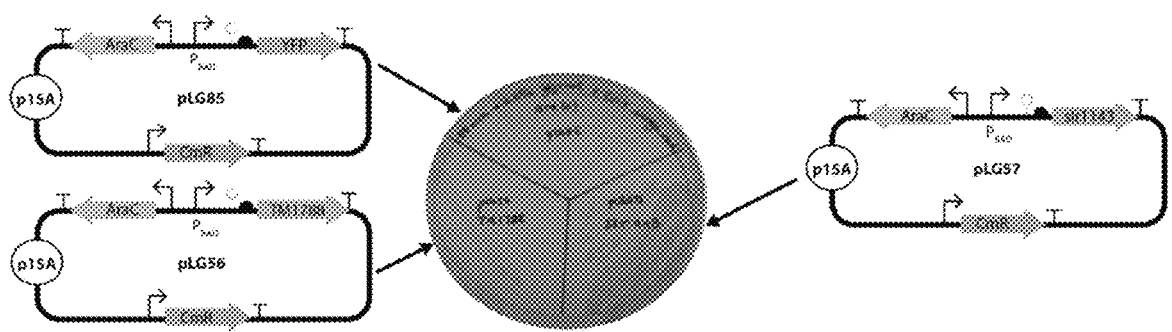
FIG. 2. Overexpression of diguanylate cyclase. The shown plasmid are expressed in *E. coli* BL21 (a) control plasmids expressing YFP. Plasmid expressing (b) an TM1788 gene from *T. maritima* and (c) an slr1143 gene from *Synechocystis* sp. (strain PCC 6803).

It is hypothesized that upregulating the production of a dgc gene in G. xylinus would yield higher production. The enzyme, diguanylate cyclase catalyzes the conversion of two guanosine triphosphate (GTP) into cyclic di-GMP[32] (c-di-GMP). The signaling molecule c-di-GMP, also present during biofilm formation, is known to activate the BscA-BscB protein complex by interacting with a PilZ domain, displacing a gating loop and opening the active site. As shown in FIG. 2, expressing the slr1143 (more prominent production) and the TM1788 genes upregulates production of amyloid fibrils in E. coli BL21 and as demonstrated through a congo red assay.

Figure 3A:
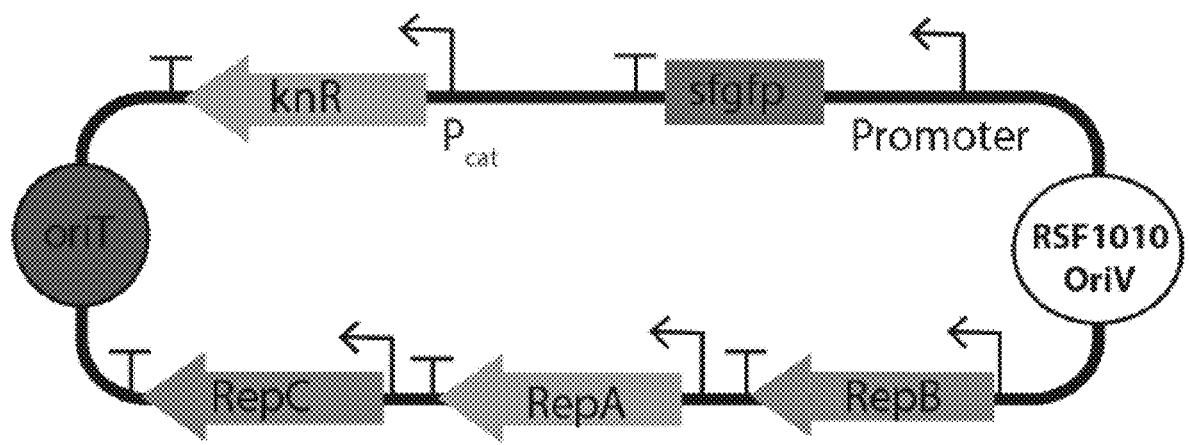
FIGS. 3a-3c. Genetic engineering tools to work with *G. xylinus*.

Slow bacterial growth is a significant limiting factor when scaling up product for commercialization, therefore, engineered a strain that grow much faster will benefit the industry. By expressing the slr1143 gene with effective promoters (FIGS. 3a and 3b) that work well with G. xylinus, more cellulose is produced, and at the same time the growth rate is increased significantly, improved by 4 times (FIG. 4, SEQ ID NO 1 and NO 2). Due to an improved electroporation method for transforming the cells, this transformation is possible (FIG. 3c).

Figure 3B:
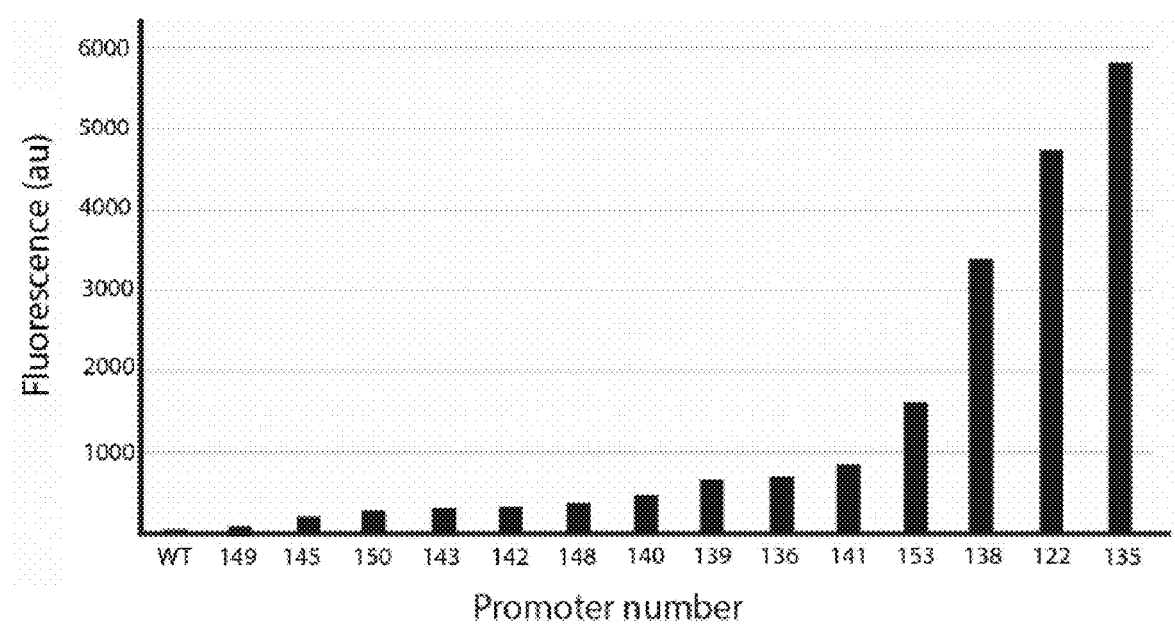
Figure 3C:
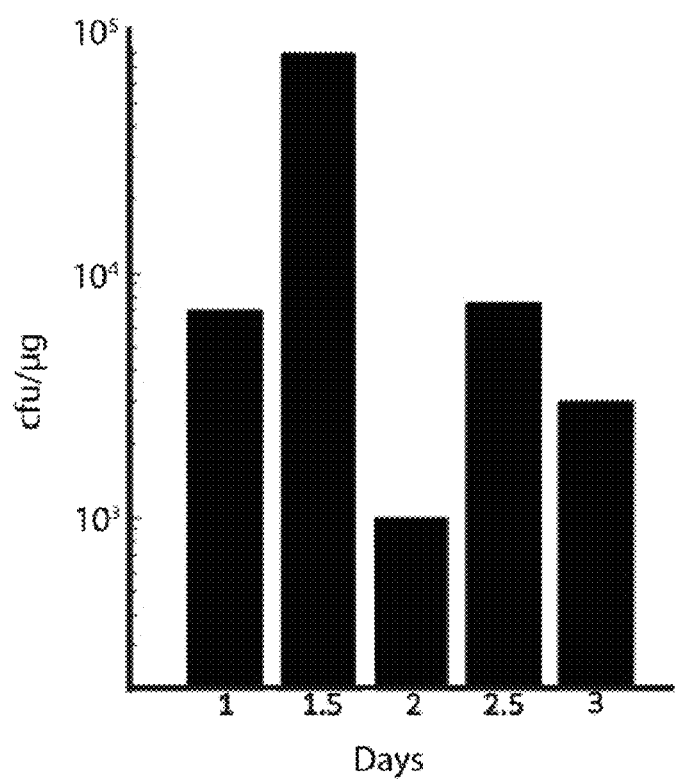
Figure 4A:
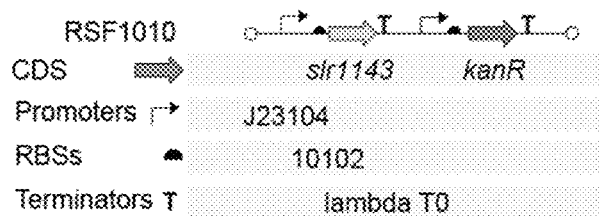
FIGS. 4a-4c. Improvement in growth rate curve and cellulose production of *G. xylinus
Figure 4B:
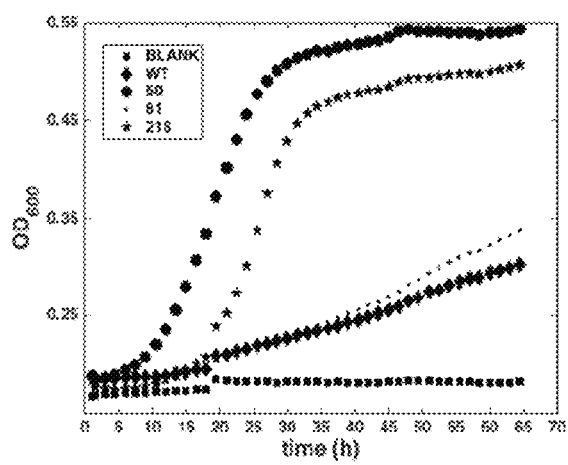
Figure 4C:
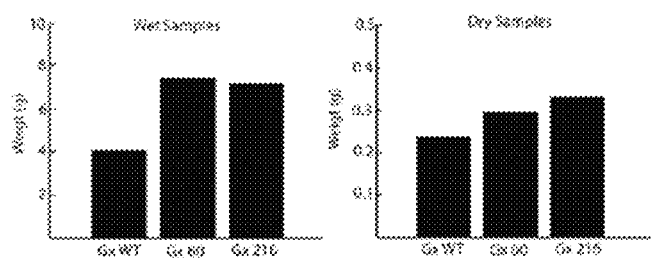

In addition, the Anderson promoters were tested, first in E. coli then in G. xylinus cells shown in FIG. 3b, so as to tune the expression of this dgc genes. Multiple broad host vectors were tested and it was found that the one with a RSF1010 origin is able to replicate in agreement with the literature. Different antibiotics were tested and it was found that tetracycline, kanamycin, spectinomycin and ampicillin are good antibiotic candidates for selection whereas chloramphenicol and gentamycin are not. G. xylinus seems to have developed natural resistance to these antibiotics.

Processing of Cellulose Materials for Various Applications

Figure 5:
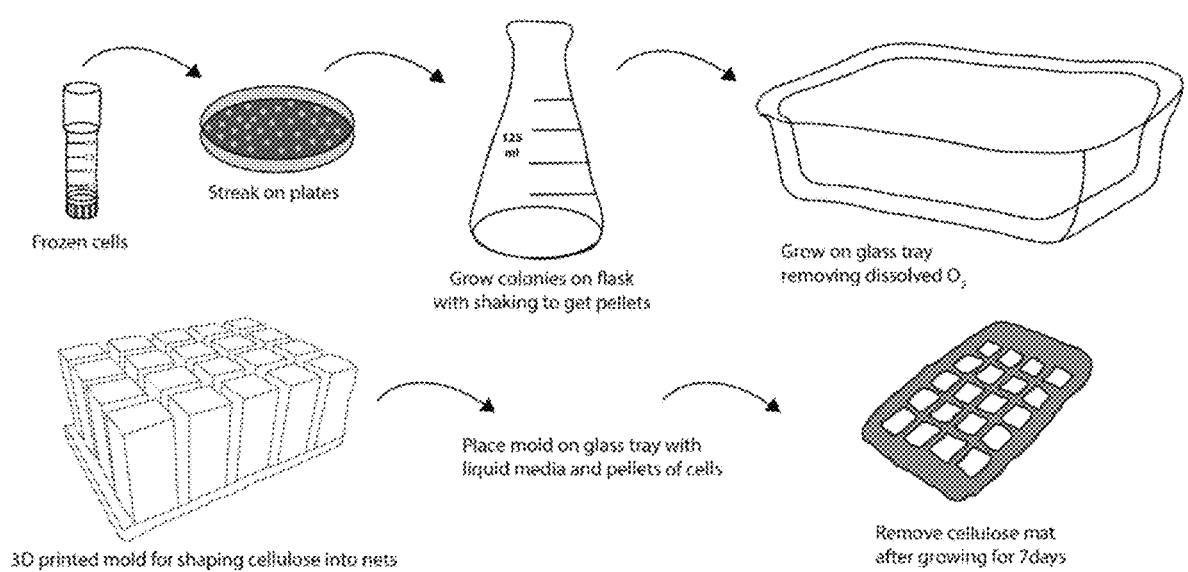
FIG. 5. Workflow for growing the *G. xylinus* cells and obtaining molded 3D printed nets.

After the cellulose materials is dried, the material become fragile and breaks easily. Flexible cellulose sheets were produced by submerging and drying the material in a plasticizer glycerol (<5%). As shown in FIG. 5, the material is grown on glass trays, then the cells are removed with 2.5% NaOH, then rinse with water and bleach. The material is subsequently washed and submerged in glycerol and let dry in metal racks. A glycerol content of 0.5 or 1% results in a smooth, cleaned (not sticky) texture. This will facilitate the usage of the material in a sewing machine. The resulting material can have dual functionality. It can be used as a biodegradable and composable plastics material when a single or thin layer is utilized. It can be used as a green vegan leather material when the layers have been stacked together. They material becomes stronger with the addition of layers. The applications for these ranges from leather bags and jackets, upholstery, footwear, clothing and automobile leather seats. Additionally, the cellulose material can be grown in a mold with a 3D printed grids (FIG. 5) to make nets for sporting goods, fishing nets, military cargos nets, safety nets, nets/mesh for packaging fruits, nature netting for trees (birds, mosquito) and medical nets.

3.5X Reduction in Media Cost and Optimization of Media

Figure 6:
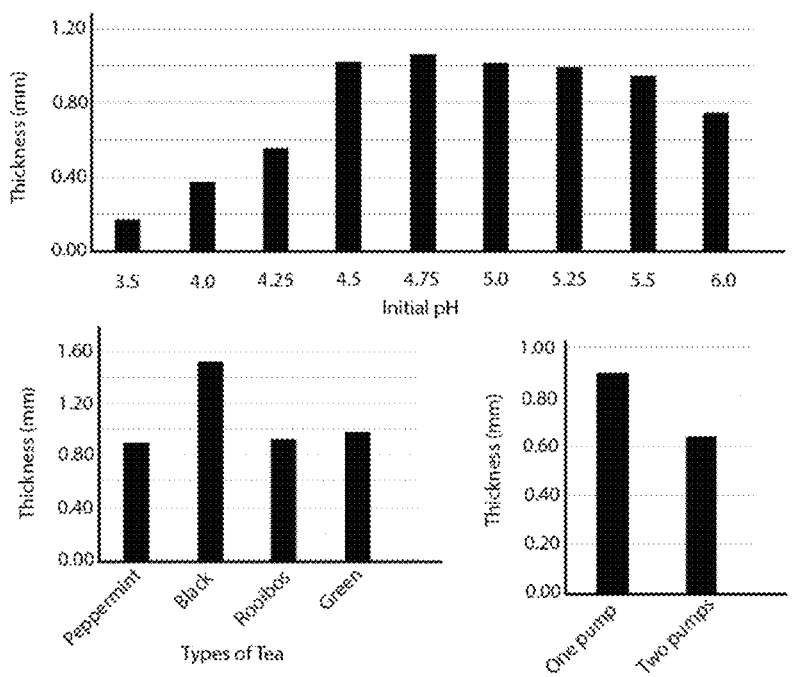
FIG. 6. Simple media optimization of pH, tea type and oxygen content.

A simple SCOBY media (present a 3.4× reduction in cost compared to the Hestrin Schram (HS) regularly used in academic labs) in the literature was modified significantly so that the cells produce thicker cellulose mat in less time (Table 1). It was found that an initial pH of 4.75 is ideal and black tea works best (FIG. 6). In addition, pumping air into the trays does not help with getting the cells to produce more cellulose. Cellulose production starts when the oxygen in the trays is completely depleted, but a high concentration of cells must be provided. The cells can be grown to a high density in shaking flasks then transferred to the trays.

TABLE 1

Cost comparison of the SCOBY media and the Hestrin and Schramm (HS)

| Ingredients | HS | K |
|---|---|---|
| Apple Cider Vinegar | | 0.38 |
| 1 Green tea bag | | 0.1 |
| Sugar | | 0.3 |
| SCOBY | | — |

TABLE 1-continued

Cost comparison of the SCOBY media
and the Hestrin and Schramm (HS)

| Ingredients | HS | K |
|---|---|---|
| Glucose | 0.25 | |
| yeast extract | 1.07 | |
| peptone | 1.84 | |
| Na2HPO4 | 0.14 | |
| CITRIC acid | 0.21 | |
| Cost (1L) | $3.51 | $0.78 |

Transferring the gas vesicle machinery, the gvp gene cluster to *B. subtilis* making it functional and optimize the number of vesicles in the cells.

Figure 7:
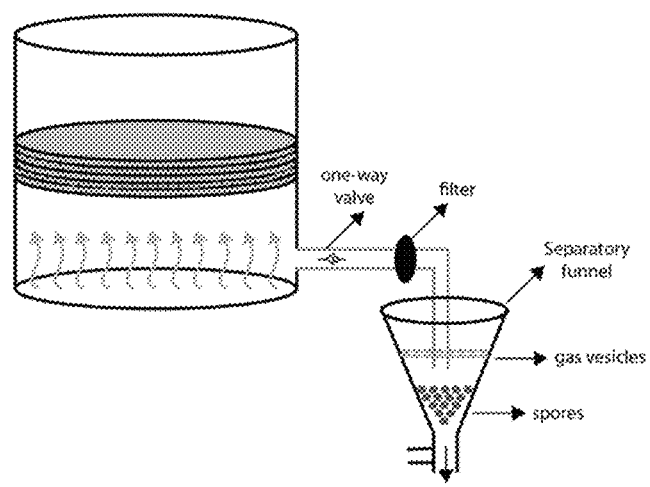
FIG. 7. Flow of the process for assembling the hybrid cellulose and gas vesicles materials.

*H. salinarum* doubles every 1.5 to 3 h and *B. subtilis* and *E. coli* double every 20 min when grown in Luria-Bertani broth (LB) at 37° C., under shaking conditions. This piece of information tells us that it impractical to use *H. salinarum* as our chassis for producing gas vesicles. This work requires the transferring of the gvp gene cluster to *B. subtilis* PY79 using readily available genetic tools. *B. subtilis* was chosen because is generally recognized as safe (GRAS status), grows fast, require minimum nutrients, has an efficient secretion system and can sporulate. In regard to exploiting sporulation, the downstream processing for separating the gas vesicles from the cells can be facilitated by inducing sporulation. Ideally, gasses will rise to the surface and spores will sink to the bottom of a separatory funnel (see FIG. 7). After spores and cell debris at the bottom have been discard, the gasses left behind, floating at the surface of the funnel can be pumped to another container having the cellulose mat at the surface. Due to buoyancy of the gas vesicles, they once again will rise and lodge into the cellulose mat. In subsequent steps in the process, while the *G. xylinus* cells are weaving the cellulose fibers, the gas vesicle will be incorporated. Alternative, the hybrid material can be created in a layer by layer fashion by alternating dipping the material between a gas vesicle bath and the growth media. Either of these methods will create a highly porous cellulose material.

Figure 8:
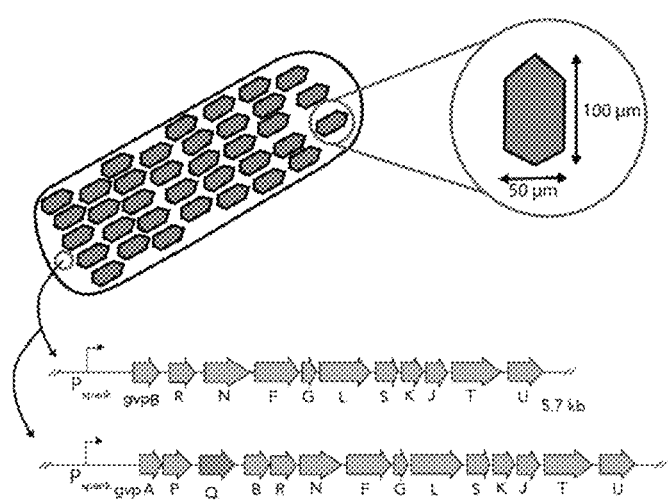
FIG. 8. Gyp cluster from *B. megaterium* and responsible for producing gas vesicles with the minimum sized (5.7 kb) and the entire cluster (7.0 kb).

The 7.0 kb gvp gene cluster (FIG. 8) found in *B. megaterium* will be integrated into the genome of *Bacillus subtilis* PY79 by homologous recombination via natural transformation (DNA uptake). In *B. megaterium*, this cluster is not functional as it might be induced under certain not known conditions. New inducible promoters were developed that can be used to tune the expression level of this gene cluster. This cluster was previous moved to *E. coli*, but only the formation of bicones (first steps in gas vesicle formation) was achieved. The natural RBSs used in this work might not be properly translated in *E. coli*. Adequate expression of gas vesicles within the *B. subtilis* PY79 cells can be scrutinized via the buoyancy phenotype, TEM micrographs and phase contrast imaging (PCI) as these vesicles are refractile bodies (appearing as bright spots). The sequence with the gyp gene cluster for expression in *B. subtilis* is included in SEQ ID NO 3. To find out more about this gene cluster, a BLAST search was conducted using the gvpQ gene and protein sequences, but no homology to other gvp genes was found. The software RADAR was used and it was determined that the gvpQ gene has 5 repeats so this might be the gvpC equivalent in other organisms. This can be tested by measuring the strength of the vesicles with and without this gene. This can be done using a pressure nephelometry to determine the critical collapsing pressure of these gas vesicles. Scrutinizing and obtaining a basic understanding of this gene cluster will contribute to basic science and further understanding of these compartments can open new fields of inquiries and lead to new discoveries. Furthermore, screening for mutant cell producing gas vesicles with higher hydrostatic pressure would be useful.

To recover the gas vesicles the method used is cell lysis by inducing sporulation. The potential of gas vesicles disintegration (through protein degradation) due to specific proteases present in the cells for protein turnover is an issue. To circumvent this natural process, a protease deficient strain of *B. subtilis* K07 (available at BGSC) can be used. The parent strain for this strain is PY79 and it has seven proteases knockout. This will allow recovery of the gas vesicles passively (not requiring centrifugation), using an economical lysing method to release the vesicles.

Part 2: Add CBD to the Gas Vesicles to Effectively Anchor them to the Cellulose Fibers Modify the Structural Protein to Display the Cellulose Binding Domain (CBD)

Figure 9A:
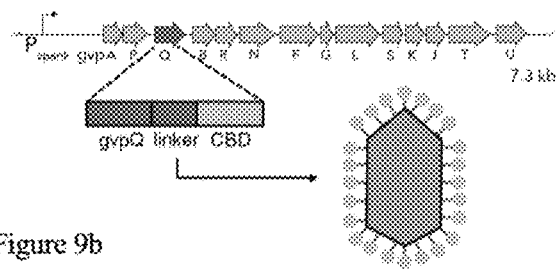
FIGS. 9a-9c. Adding a cellulose binding domain (CDB to the gas vesicles).
Figure 9B:
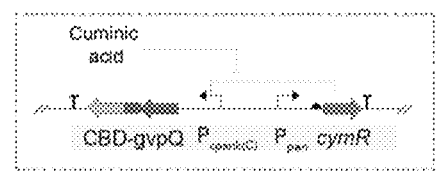
Figure 9C:
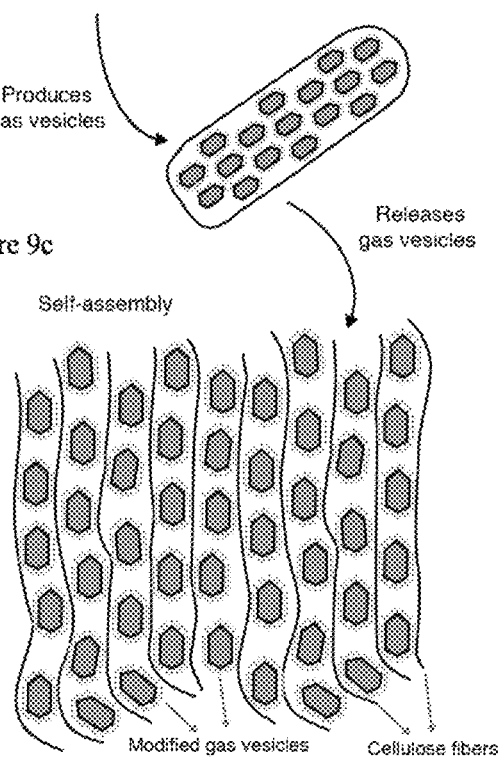
Figure 10A:
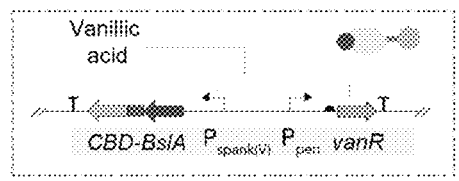
FIGS. 10a-10c. Transforming the cellulose mat into a hydrophobic material through genetically engineering.
Figure 10B:
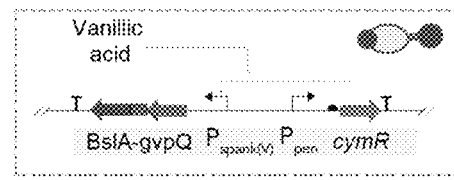
Figure 10C:
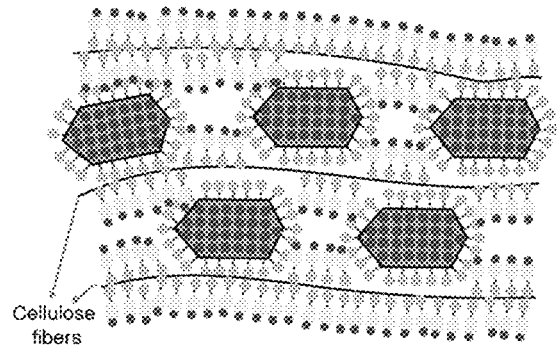

The addition of the gas vesicles to this material should significantly raise the R-value by reducing the solid portion and thus decreasing the heat transfer through the cellulose. To incorporate and secure the gas vesicle effectively within the cellulose network, genetic engineering tools can be used to link the C-terminus of the structural protein, GvpC or the equivalent, GvpQ, in the gas vesicles to a cellulose binding domain (CBD) or cellulose binding module (CBM) (FIG. 9, SEQ ID NO 4). CBD are usually found in enzyme that required docking (for close proximity) in order to execute a function. Specific CBM family include the CBM47 and CBM48. Examples are CBM48 from *Komagataeibacter sucrofermentans* and *Micromonas pusilla*. For example, cellulase from *Trichoderma reesei* is an enzyme with a CBD linked via a peptide to a catalytic domain (CD). Adding CBD should allow anchoring of these gas vesicles to the cellulose fibers. A *B. subtilis* strain capable of producing these genetically modified gas vesicles can be manipulated to create bicone shaped vesicles (the initial step in their biogenesis of gas vesicles) to limit the size of these compartments for reduced convective heat transfer through the vesicles.

Another technical challenge is to modify the vesicles without compromising their structural integrity. By controlling the expression level of the gvpQ-CBD hybrid protein, the correct level of expression to maintain the structural integrity can be assayed. To prevent steric hindrance, misfolding and low protein yield and to effectively create this multidomain protein, various polypeptide linkers, (GSSGSS)n, (GSSSSS)n, (SSSSSS)n and (GGGGGG), can be placed between the GvpQ and CBD. To promote intermolecular reaction between the gas vesicles and the fibers, the length of the linkers can be varied(n=1–4). The shorter the linker the more hydrophobic as there are less hydrophilic moieties exposed, therefore when doing this assessment, the shorter ones may be best if binding is not compromised. The last step in the process is to collect the modified gas vesicles and incorporate them while growing the cellulose mat as in FIG. 9. To non-destructively inspect the size of the pores, X-ray computed tomography, typically used for examining gas holes in swiss cheeses, can be used. This vesicles can be also inspected through SEM and TEM.

Test the R-Value of the Material.

To show feasibility the thermal conductivity of this hybrid material must be measured. For comparison, at room temperature vacuum has a thermal conductivity ($\lambda$) equals 0.001 W/mK and on the other side of the spectrum there is diamond with a $\lambda$=2000 W/mK. In building technology, the terms λ is shown as a thermal resistance. This is denoted by R-value (British system units) or RSI (SI system units) which expresses the thickness of the sample divided by A. The higher the R-value the slower the rate of heat transfer through the insulation material. Using a heat flowmeter (Netzsch HFM 436 lambda), the thermal conductivity of the initial material (not processed) which is bare bacterial cellulose was measured as wet and dry sheets with λ equal to 0.31 W/mK (comparable to soil) and 0.15 W/mK (comparable to dry plywood). The R-values equivalent for the wet and dry sheets are 0.46 and 0.93 ft$^{2\circ}$ F. h/Btu in one inch, respectively. For this material to be competitive, it should have an R-value/in circa R-6. This will make the material competitive with spray foam on top of adding the green and sustainability aspect. Below, and improved method is outlined.

Adding Holes to the Cellulose Materials to Increase the R-Value

A procedure to clean the cellulose, remove the cells, and dry it was implemented. The R-value of the resulting material with two different treatments was measured. The first sample was simply a rectangular sample of several stacked layers of the cleaned cellulose.

For the second treatment holes (diameter ~2 mm) were punched in sheets of the material using a custom-built device for high throughput. The printed device consists of a 3D printed 8"×6" holder for multiple push-pins spaced about ⅕ inch (5 mm) apart. Each sheet was punched multiple times in different orientations to create hundreds of "randomly" arranged holes. The last step of making this sample consisted of stacking rectangular cutouts of the sheets so that the holes did not line up in different layers.

The measured R-value for Sample 1 (simple stacking) was 1.78. The measure R-value for Sample 2 (layers with holes) was 3.27, which is nearly as high the R-value of fiberglass insulation, which is about 3.5. By adding the GVs, materials with even higher values (with nanopore sized) can be produced. Furthermore, as a risk mitigation strategy, optimizing the size and arrangement of punched holes in multiple layers could lead to a cost competitive material with high R-value even without the addition of gas vesicles as these materials are green.

Adding a cocktail of protease inhibitors would prevent GVs from getting degraded by *G.xylinus* proteases before getting incorporated and shaping the cellulose mat. The GVs after purification and resuspension in 1×PBS are mixed with 2X SCOBY media in a 1:1 ratio with the inoculum of *G. xylinus* cells grown for 3 days (when using the WT strain). The mixture of the WT cells, media and GVs are grown for 8 days on square plates. After this the mat is cleaned with 2.5% NaOH and bleach before folding over multiple times. Other scaffolding material could be used in the process especially grown material such as mycelium cells. Other scaffolding materials include silk, down, leather, fur, wool, polyester, polyhydroxyalkanoates (PHAs) and silica. A linker module needs to be present to promote attachment of these scaffolding materials to the GVs.

Part #3: Genetically Engineering Hydrophobicity and Fire-Retardant Properties into the Fibers.

Making the Cellulose Fibers Hydrophobic by Coating the Fibers with CBD-Hydrophobin.

For this material to be a multifunctional insulation material, its hydrophobicity or vapor barrier capability must be confirmed. Keeping a wall sections dry is a critical property of any building insulation material to prevent the growth of mold. If the addition of the gas vesicles does not provide sufficient vapor barrier performance, modification of the vesicles' coating through genetic engineering will be needed. This modification might need to be done only on the surface of the material and not within the material. A candidate with a hydrophobic cap is the protein, BslA, which would mask the small hydrophilic protein, GvpQ on a gas vesicle. The BslA proteins forms an elastic film in an air-water interphase.

In addition to covering the gas vesicles, it is helpful to cloak the hydrophilic cellulose fibers. A genetic circuit has been designed to do this using the same BslA protein (FIG. 11, SEQ ID NO 5). Other hydrophobins can be screened to find the right candidate suited for this application. The candidates hydrophobins include HFBI, EAS, DewA, chaplins, SapB, SapT, cryparin and HypA.

*B. subtilis* is known for its ability to secrete large quantities of protein (20-25 g/L have been reported) and has been used widely in industry. Considering this, *B. subtilis* can be used as a workhorse for producing and secreting out this coating enzyme. Enzymes targeted for secretion contain a signaling peptide (SP), and are translocated to the secretion machinery. Once the surface has been modified with these engineered proteins, they can be tested using contact angle measurements. A contact angle greater than 120° would make this material fall in the hydrophobic range. This measurement can be done through using an optical tensiometer device.

Modify the Fibers to be Fire-Resistant with Melanin Materials

Untreated cellulose with high porosity is a potential fire hazard. To comply with building fire codes, treatment of our material with boric acid, halogenated anilines, or brominated compounds (BRFs) would bring it into compliance with building fire codes. However, to avoid or reduce these environmentally problematic treatments, bacterial produced melanin to enhance the flame-retardant properties of our materials can be explored. Melanin resembles synthetic polydopamine, which other researchers have shown to be useful as a fire retardant. A tyrosinase enzyme can be expressed to form melanin in *B. subtilis* and create a composite polymeric material of cellulose and melanin at the surface of the material as a protective layer. Testing can determine if this composite material will char, sequester free radicals, and consequently stop the spread of fire.

CONCLUSION

It is expected that the degree of entanglement and packing density is important, as the nanoporosity of the network is important to obtaining a material with a high R-value. The cellulose network will act as a carrier for the interweaved gas vesicles which brings about the nanoscale porosity to the network. At the cellulose-medium interfaces the hydrophobins, BslA or HFBI could impart the hydrophobicity properties needed to keep this material from getting wet (antimicrobial properties) and to preserve the insulation properties. In addition to moving genes to another more suitable chassis, genetically engineering tools are useful because instead of adding expensive chemicals for surface modification (e.g. adding hydrophobicity), those changes can be introduced at the genetic level. In the future, the capabilities of gas vesicle to dampen sound due to the ability of gas vesicles to scatter sound waves and other applications for this cutting-edge research can be explored. These applications encompass hydrophobic clothing and thin lining for coats and vehicles (transportation), oil spills cleanups, cosmetics, acoustic insulation, filtration, packaging materials and thermal shielding for extreme cold and hot environments (deep ocean, artic and space explorations).

Examples of the materials, strains, systems, methods and apparatuses discussed herein are not limited in application to the details of construction and the arrangement of components set forth in the following description or illustrated in the accompanying drawings. The systems, methods and apparatuses are capable of implementation in other examples and of being practiced or of being carried out in various ways. Examples of specific implementations are provided herein for illustrative purposes only and are not intended to be limiting. In particular, functions, components, elements, and features discussed in connection with any one or more examples are not intended to be excluded from a similar role in any other examples.

Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

Also, the phraseology and terminology used herein is for the purpose of description and should not be regarded as limiting. Any references to examples, components, elements, acts, or functions of the computer program products, systems and methods herein referred to in the singular may also embrace embodiments including a plurality, and any references in plural to any example, component, element, act, or function herein may also embrace examples including only a singularity. Accordingly, references in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A material comprising:
    a scaffold comprising a series of at least partially spaced bacterial-derived cellulose fibers produced by genetically modified *G. xylinus* bacteria with an upregulated dgc gene; and
    bacterial-derived gas vesicles produced by a-genetically modified *B. subtilis* bacteria and comprising GvpA and GvpC proteins, and located between fibers, wherein the gas vesicles comprise integral external anchoring modules that comprise cellulose binding modules that comprise CBM48, wherein the external anchoring modules are effective to link the gas vesicles to the bacterial cellulose fibers:
    wherein at least some of the gas vesicles have lengths from 0.1 to 2 microns.

2. The material of claim 1, comprising an aerogel.

3. The material of claim 1, wherein the gas vesicles further comprise a bacterial-derived external hydrophobicity coating that comprises the BslA protein.

4. The material of claim 1, wherein the cellulose fibers further comprise bacterial-derived melanin to provide fire resistance.

* * * * *